United States Patent
Moriwaki et al.

(10) Patent No.: US 11,155,705 B2
(45) Date of Patent: Oct. 26, 2021

(54) UNSATURATED GROUP-CONTAINING ESTER COMPOUND, POLYMER, THERMOSETTING RESIN COMPOSITION, AND CURED FILM

(71) Applicant: KYOEISHA CHEMICAL CO., LTD., Osaka (JP)

(72) Inventors: Yuya Moriwaki, Nara (JP); Kosuke Asada, Nara (JP); Masaru Donkai, Nara (JP); Naomi Takenaka, Nara (JP)

(73) Assignee: KYOEISHA CHEMICAL CO., LTD., Osaka (JP)

( * ) Notice: Subject to any disclaimer, the term of this patent is extended or adjusted under 35 U.S.C. 154(b) by 63 days.

(21) Appl. No.: 16/379,917

(22) Filed: Apr. 10, 2019

(65) Prior Publication Data
US 2019/0284385 A1   Sep. 19, 2019

Related U.S. Application Data

(63) Continuation-in-part of application No. PCT/JP2019/000469, filed on Jan. 10, 2019.

(30) Foreign Application Priority Data

Jan. 15, 2018 (JP) .............................. JP2018-004111
Jul. 31, 2018 (WO) ................... PCT/JP2018/028559

(51) Int. Cl.
*C08F 8/14* (2006.01)
*C08L 33/14* (2006.01)
(Continued)

(52) U.S. Cl.
CPC .............. *C08L 33/14* (2013.01); *C07C 69/54* (2013.01); *C07C 69/67* (2013.01); *C08F 8/14* (2013.01); *C08F 20/10* (2013.01); *C08F 20/26* (2013.01); *C08K 5/0025* (2013.01); *C08K 5/053* (2013.01); *C08L 33/04* (2013.01); *C08L 2203/16* (2013.01)

(58) Field of Classification Search
CPC .......... C08F 220/06; C08F 20/10; C08F 8/14; C08L 33/08; C08L 33/04; C08L 33/14
See application file for complete search history.

(56) References Cited

U.S. PATENT DOCUMENTS 4,897,450 A   1/1990   Craun et al.
4,906,693 A   3/1990   Craun et al.
(Continued)

FOREIGN PATENT DOCUMENTS

EP   3 623 423 A1   3/2020
EP   3 623 424 A1   3/2020
(Continued)

OTHER PUBLICATIONS

USPTO structure search, Dec. 2020.*
Ayres, Lee, et al., "Elastin-Based Side-Chain Polymers Synthesized by ATRP", Macromolecules 2003, 36, 5967-5973.
Huynh, Vien T., et al., "Block Copolymer Micelles with Pendant Bifunctional Chelator for Platinum Drugs: Effect of Spacer Length on the Viability of Tumor Cells", BioMacromolecules, 2012, 13, American Chemical Society, pp. 1010-1023.
Japanese Office Action corresponding to Japanese Application No. 2019-506741, dated Jun. 25, 2019.
European Search Report, dated Mar. 12, 2021, corresponding to EP Application No. 19738507.3.

*Primary Examiner* — Gregory Listvoyb
(74) *Attorney, Agent, or Firm* — Ladas & Parry LLP; Malcolm J. MacDonald

(57) ABSTRACT

It is an object of the present invention to provide an unsaturated group-containing ester compound which can be used as a raw material of a curable composition using transesterification reaction and which is inexpensive and has a good curability, and a polymer, a thermosetting resin composition, and a curable composition which containing the unsaturated group-containing ester compound, respectively.

An unsaturated group-containing ester compound having a chemical structure represented by the following general formula (1):

$$\underset{R_3}{\overset{R_2}{>}}=\underset{R_4}{\overset{R_1}{<}}\text{-[COOR}_5]_{n_1} \quad (1)$$

$n_1$: 1 to 10

(in the formula, $R_1$, $R_2$, and $R_3$ are the same or different and each is a hydrogen, an alkyl group, a carboxyl group, an alkyl ester group or a structure represented by $R_4$-[COOR$_5$]$_{n_1}$;

$R_4$ is an aliphatic, an alicyclic or an aromatic alkylene group with a number of atoms of 50 or less in the main chain, which may have one or more functional groups selected from the group consisting of an ester group, an ether group, an amide group, and a urethane and may have a side chain;

$R_5$ is an alkyl group having 50 or less carbon atoms; and in the compound represented by the general formula (1), the $R_4$-[COOR$_5$] group may be a lactone structure represented by the following general formula (1-1).

$$\underset{R_3}{\overset{R_2}{>}}=\underset{R_4}{\overset{R_1}{<}}\left(\text{-R}_x\underset{O}{\overset{O}{<}}\right)_{n_1} \quad (1\text{-}1)$$

($R_x$ is a hydrocarbon group having 2 to 10 carbon atoms which may have a branched chain.)

12 Claims, 18 Drawing Sheets

(51) Int. Cl.
*C08F 20/26* (2006.01)
*C08K 5/00* (2006.01)
*C07C 69/67* (2006.01)
*C07C 69/54* (2006.01)
*C08F 20/10* (2006.01)
*C08L 33/04* (2006.01)
*C08K 5/053* (2006.01)

(56) References Cited

U.S. PATENT DOCUMENTS

| | | |
|---|---|---|
| 2003/0162904 A1 | 8/2003 | Lachowicz et al. |
| 2012/0140008 A1* | 6/2012 | Ganapathiappan ... C08F 220/28 347/102 |
| 2013/0233739 A1 | 9/2013 | Zhao et al. |
| 2014/0265031 A1 | 9/2014 | Yoshida et al. |

FOREIGN PATENT DOCUMENTS

| | | |
|---|---|---|
| JP | 2-147675 | 6/1990 |
| JP | H02288844 A | 11/1990 |
| JP | H0892503 | 4/1996 |
| JP | 09-59543 A | 3/1997 |
| JP | H09302271 | 11/1997 |
| JP | H09302274 A | 11/1997 |
| JP | 2000267286 A | 9/2000 |
| JP | 2003119401 A | 4/2003 |
| JP | 2004-217857 | 8/2004 |
| JP | 2007-100108 A | 4/2007 |
| JP | 2014-172333 A1 | 9/2014 |
| JP | 2018-44056 A | 3/2018 |

\* cited by examiner

UNSATURATED GROUP-CONTAINING ESTER COMPOUND, POLYMER, THERMOSETTING RESIN COMPOSITION, AND CURED FILM

TECHNICAL FIELD

The present invention relates to an unsaturated group-containing ester compound, a polymer, a thermosetting resin composition, and a cured film.

BACKGROUND OF THE DISCLOSURE

In the fields of a coating and an adhesive, various thermosetting resin compositions are used. In many of such thermosetting resin compositions, a resin having two or more hydroxyl groups is used in combination with a curing agent and the resin is cured by a crosslinking reaction between the curing agent and the hydroxyl group.

As the curing agent, melamine resins, epoxy compounds, and polyisocyanate compounds are used. These curing agents are widely and generally used because the curing agents have a good thermal reactivity and cured resins obtained by using the curing agent have superior characteristics. However, the melamine resin is presumed as the cause of sick house syndrome because it generates formaldehyde, so that it has been restricted in uses. In addition, if it is used in a coating, a problem in acid resistance is known to occur because of its chemical structure.

Epoxy compounds are said to have a low storage stability and a high curing temperature, though they are high in curability and coating film properties. Polyisocyanate curing system is said to show a narrow range of design though it is high in curability and coating film properties. Therefore, a coating composition which has a high curability and a wide range of design to develop the desired coating film properties, and does not by-produce harmful substances is required.

Patent document 1 discloses a powder coating using a transesterification reaction as a curing reaction. However, in this invention, it is merely described that a curing reaction by transesterification is carried out using a resin having both a (meth)acrylate-derived backbone and a hydroxyl group, but a compound having another alkyl ester group does not been studied.

Patent document 2 discloses a coating using a transesterification reaction as a curing reaction. In this document, a detailed composition of the resin to be used is not restricted, and a composition which can be suitably used for a curable composition through a transesterification reaction is not identified. Also, no investigation has been made as to what type of alkyl ester group is used to obtain good curing reactivity.

On the other hand, as a compound having an unsaturated bond and an alkyl ester bond, there are many well-known compounds. However, many of the unsaturated bonds and alkyl ester bonds are present in relatively close proximity to each other, and no investigation has been made on alkyl ester compounds in which these bonds are bonded via a linking group having a certain number or more of molecular numbers. Further, no study has been made on the use of this compound in a thermosetting resin composition using a transesterification reaction as curing reaction.

Most of thermosetting resin compositions are generally thermally cured at 150° C. or higher. If the curing reaction temperature can be lowered, energy cost in the coating process can be lowered, which is useful as a cost reduction technique. Furthermore, in the coating of plastic products, since coating at a lower temperature is required, a thermosetting resin composition which is of low temperature curing type is required.

Further, with respect to the primary and secondary alkyl esters, the curing reaction rate is said to be slower than the tertiary alkyl ester. Therefore, in order to obtain a thermosetting resin composition by a transesterification reaction using primary and secondary alkyl ester groups, it is required to increase the curing reaction rate.

PRIOR TECHNICAL DOCUMENTS

Patent Documents

[Patent Document 1] Japanese Kokai Publication Hei9-59543

[Patent Document 2] Japanese Kokai Publication Hei2-147675

SUMMARY OF INVENTION

Problems to be Solved by the Invention

In view of the above, it is an object of the present invention to provide an unsaturated group-containing ester compound which may be used as a raw material for a thermosetting resin composition having a good transesterification reactivity, and a polymer, a thermosetting resin composition, and a cured film using the same as a raw material, respectively.

Means for Solving Object

The present invention relates to an unsaturated group-containing ester compound having a chemical structure represented by the following general formula (1).

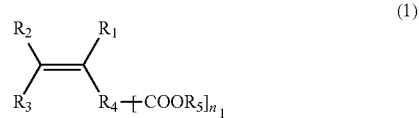

$n_1$: 1 to 10

(in the formula, $R_1$, $R_2$, and $R_3$ are the same or different and each is a hydrogen, an alkyl group, a carboxyl group, an alkyl ester group or a structure represented by $R_4$-[COOR$_5$]; $R_4$ is an aliphatic, an alicyclic or an aromatic alkylene group with a number of atoms of 50 or less in the main chain, which may have one or more functional groups selected from the group consisting of an ester group, an ether group, an amide group, and a urethane and may have a side chain; $R_5$ is an alkyl group having 50 or less carbon atoms; and in the compound represented by the general formula (1), the $R_4$-[COOR$_5$] group may be a lactone structure represented by the following general formula (1-1).

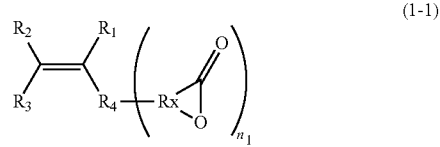

($R_x$ is a hydrocarbon group having 2 to 10 carbon atoms which may have a branched chain.)

The unsaturated group-containing ester compound preferably have a chemical structure represented by the following general formula (2).

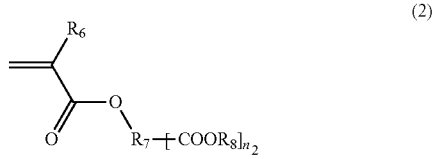
(2)

$n_2$: 1 to 10
(in the formula, $R_6$ is H or a methyl group; $R_7$ is an alkylene group with a number of atoms of 48 or less in the main chain, which may have an ester group, an ether group and/or an amide group in the main chain, and may have a side chain; and
$R_8$ is an alkyl group having 50 or less carbon atoms.)

In the unsaturated group-containing ester compound, $R_5$ and/or $R_8$ is preferably a tertiary alkyl group.

The present invention relates to a polymer (A) containing a structural unit derived from the above-mentioned unsaturated group-containing ester compound in at least a portion thereof.

The present invention relates to a polymer (C) containing a structural unit derived from the above-mentioned unsaturated group-containing ester compound and a structural unit derived from a hydroxyl group-containing unsaturated monomer as essential constituting unit.

The structural unit derived from the hydroxyl group-containing unsaturated monomer preferably contains a structural unit derived from the monomer represented by the following general formula (4) in at least a portion thereof.

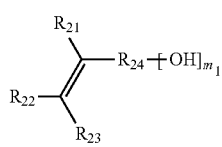
(4)

$m_1$: 1 to 10
(in the formula, $R_{21}$, $R_{22}$, and $R_{23}$ are the same or different and each is a hydrogen, an alkyl group, a carboxyl group, an alkyl ester group or a structure represented by the following $R_{24}$-[OH]$m_1$;
$R_{24}$ is an aliphatic, an alicyclic or an aromatic alkylene group with a number of atoms of 3 to 50 in the main chain, which may have one or more functional groups selected from the group consisting of an ester group, an ether group, an amide group, and a urethane and may have a side chain.)

The present invention relates to a thermosetting resin composition comprising the above-mentioned polymer (A), a hydroxyl group-containing compound (B) with at least two hydroxyl groups, and a transesterification catalyst (F).

The hydroxyl group-containing compound (B) is preferably a polymer containing a structural unit derived from the monomer represented by the above general formula (4) in at least a portion thereof.

The present invention relates to a thermosetting resin composition comprising the above-mentioned polymer (C) and a transesterification catalyst (F).

The present invention relates to a cured film formed by three-dimensionally crosslinking the above-mentioned thermosetting resin composition.

Effects of the Invention

The present invention relates to a new unsaturated group-containing ester compound, and a polymer obtained by polymerizing the compound can show an excellent curing reactivity when used in a thermosetting resin composition using a transesterification reaction as a curing reaction.

Further, the thermosetting resin composition of the present invention has an excellent low temperature curability. Therefore, a good performance that can be cured at 140° C. can be achieved, and a thermosetting resin composition curable at 120° C. or less depending on the composition, and curable at 80° C. in the case of the most preferred composition, may be obtained. Such thermosetting resin composition is preferred in that the energy cost in the thermal curing step can be reduced. It is also preferable in that it can be applied to plastic coating.

Furthermore, in the thermosetting resin composition using the transesterification reaction of a compound having a primary or secondary alkyl ester, the reaction rate can be made faster than the conventional one. Consequently, it is possible to cause curing at a practically usable level, in a thermosetting resin composition utilizing the transesterification reaction of the compound having a primary or secondary alkyl ester, which is considered to be difficult to put into practical use.

In addition, the resin having an alkyl ester group based on the structure as in the present invention reduces foaming during curing. Therefore, it is preferable also from the viewpoint of preventing deterioration of appearance due to foaming

BRIEF DESCRIPTION OF THE DRAWINGS

FIG. 13 is a rigid body pendulum data at 140° C. of Comparative Example 5.

DETAILED DESCRIPTION OF PREFERRED EMBODIMENTS

Figure 1:
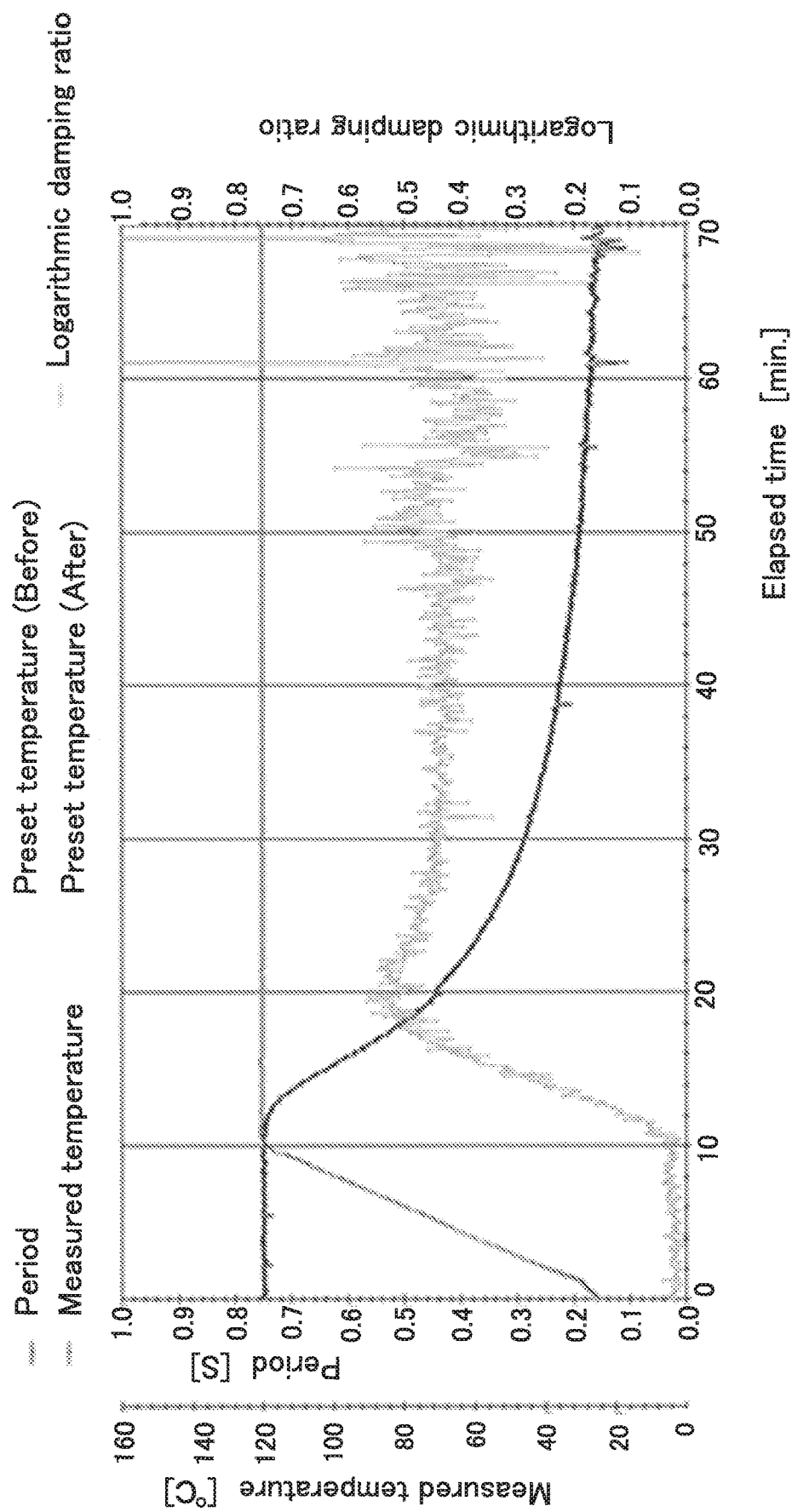
FIG. 1 is a rigid body pendulum data at 120° C. of Example 1.

Hereinafter, the present invention will be described in detail.

In the following description, "(meth)acrylate" means acrylate and/or methacrylate. "(Meth)acrylic acid" means acrylic acid and/or methacrylic acid. "(Meth)acryloyl" means acryloyl and/or methacryloyl. "(Meth)acrylamide" means acrylamide and/or methacrylamide.

(Unsaturated Group-containing Ester Compound)

The present invention relates to an unsaturated group-containing ester compound having a chemical structure represented by the following general formula (1).

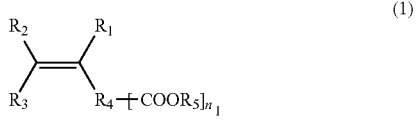

(1)

$n_1$: 1 to 10

(in the formula, $R_1$, $R_2$, and $R_3$ are the same or different and each is a hydrogen, an alkyl group, a carboxyl group, an alkyl ester group or a structure represented by the following $R_4$-$[COOR_5]n_1$;

$R_4$ is an aliphatic, an alicyclic or an aromatic alkylene group with a number of atoms of 50 or less in the main chain, which may have one or more functional groups selected from the group consisting of an ester group, an ether group, an amide group, and a urethane and may have a side chain;

$R_5$ is an alkyl group having 50 or less carbon atoms; and in the compound represented by the general formula (1), the $R_4$-$[COOR_5]$ group may be a lactone structure represented by the following general formula (1-1).

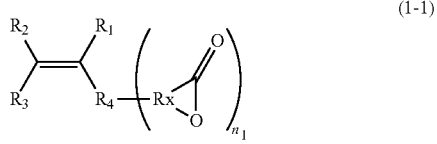

(1-1)

($R_x$ is a hydrocarbon group having 2 to 10 carbon atoms which may have a branched chain.)

A polymer may be obtained by polymerization reaction via an unsaturated bond of the above-mentioned compound. As to the polymer thus obtained, the main chain formed based on the polymerization of the unsaturated bond and the alkyl ester group are present apart via the linking group in the case that the polymer is used in a thermosetting resin composition using a transesterification reaction as curing reaction. Therefore, the alkyl ester group can move relatively freely. As a result, it has been found by the present inventors that the alkyl ester group and the hydroxyl group are easily accessible, and the reactivity of transesterification is improved. By improving the reactivity of the transesterification reaction in this manner, short-time curing and reduction in the curing temperature can be realized, and the usefulness of the thermosetting resin composition by the transesterification reaction can be enhanced.

When the alkyl ester group is a t-butyl ester group, the t-butyl group desorbed during heat curing becomes isobutene, and a gas component is generated. As a result, it has been known that bubbles are generated so that various problems such as appearance deterioration and strength reduction may be caused.

When the above-mentioned unsaturated group-containing ester compound of the present invention is used, foaming is suppressed by lowering the viscosity of the coating film during curing, and the above-mentioned problem is remarkably improved. Even in this point, the present invention has a preferable effect.

In the present invention, the alkyl ester group is not limited. However, it is more preferred to contain the tertiary alky ester group as a part or whole of the alkyl ester groups because the transesterification reaction tends to occur compared with the secondary alkyl ester group and the primary alkyl ester group, so that the reaction can be promptly carried out at low temperature. As the tertiary alkyl ester group, a t-butyl ester group is particularly preferable. In the present invention, it is particularly preferable that the alkyl ester group is a tertiary alkyl ester group such as a t-butyl ester group from the viewpoint that a faster reaction rate can be obtained than before and it can be cured at very low temperatures of 120° C. or less depending on its structure.

The alkyl ester group other than tertiary is not particularly limited, and those having known ester groups such as a methyl ester group, an ethyl ester group, a benzyl ester group, an n-propyl ester group, an isopropyl ester group, an n-butyl ester group, an isobutyl ester group, and sec-butyl ester group can be used. Incidentally, it is preferable that the alkyl group has 50 or less carbon atoms. Since the alkyl group is formed as an alcohol during the transesterification reaction and is preferably volatilized, the alkyl group is more preferably one having 20 or less carbon atoms, still more preferably 10 or less. The boiling point of the alcohol volatilizing in the curing reaction is preferably 300° C. or less, more preferably 200° C. or less.

As mentioned above, when the alkyl ester group is a tertiary alkyl ester group such as a t-butyl ester group, it is preferable because it is particularly excellent in reactivity and low temperature curability. On the other hand, even in a thermosetting resin composition that uses a transesterification reaction of primary and secondary alkyl esters as a curing reaction, which has been considered not to provide a sufficient curing reaction, use of the compound having the structure disclosed in the present invention is preferable in that good curing performance can be realized. From this point of view, even when it is a primary alkyl ester or a secondary alkyl ester, it has a remarkable effect when compared with the conventional compound.

The alkyl group in the alkyl ester group (ie, $R_5$ in the above general formula) is an alkyl group having 50 or less carbon atoms, but the number of carbon atoms is preferably within the range of 1 to 20, more preferably within the range of 1 to 10, still more preferably within the range of 1 to 6, and most preferably within the range of 1 to 4. Within such a range, it is preferable in that the curing reaction can proceed suitably.

The case where the alkyl ester group is a lactone group is also included in the present invention. The ester group of such a lactone group can also cause the transesterification reaction of the present invention and can be utilized for curing reaction. Such a compound has the chemical structure of the above (1-1).

More specifically, as the structure represented by the general formula (1), for example, the following structure may be mentioned.

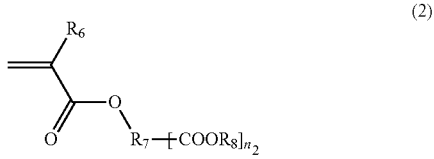

(2)

$n_2$: 1 to 10
(in the formula, $R_6$ is H or a methyl group; $R_7$ is an alkylene group with a number of atoms of 48 or less in the main chain, which may have an ester group, an ether group and/or an amide group in the main chain, and may have a side chain; $R_8$ is an alkyl group having 50 or less carbon atoms.) Such a compound is a derivative of (meth) acrylic acid and can be obtained by a known synthesis method using (meth) acrylic acid or a derivative thereof as a raw material.

The number of atoms in the main chain of $R_7$ is more preferably 40 or less, still more preferably 30 or less, and further more preferably 20 or less. The atom that may be contained in the main chain of $R_7$ is not particularly limited, and an oxygen atom, a nitrogen atom, a sulfur atom, a silicon atom and the like in addition to a carbon atom may be contained. More specifically, in the main chain of $R_7$, an ether group, an ester group, an amino group, an amide group, a thioether group, a sulfonate group, a thioester group, a siloxane group, etc. in addition to an alkyl group may be contained.

Also in the compound represented by the general formula (2), it is especially preferable to use a tertiary alkyl group for $R_8$, and most preferably to use t-butyl group.

As specific examples of structures represented by the general formula (2), for example, the compounds represented by the following general formula may be mentioned below.

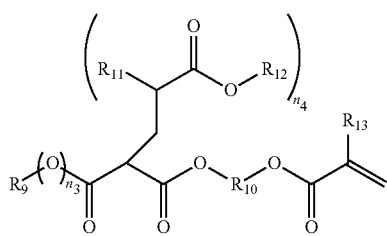

(3)

(in the formula, $R_9$ is an alkyl group having 1 to 50 carbon atoms;
$R_{10}$ is an alkylene group with a number of atoms of 44 or less in the main chain, which may have an ester group, an ether group and/or an amide group in the main chain, and may have a side chain;
$R_{11}$ is H or a methyl group;
$R_{12}$ is an alkyl group having 50 or less carbon atoms;
$R_{13}$ is H or a methyl group;
$n_3$ is 0 or 1; and
$n_4$ is 1 or 2.)

Also in the compound represented by the general formula (3), $R_{12}$ in the above general formula is an alkyl group having 50 or less carbon atoms, but the number of carbon atoms is preferably within the range of 1 to 20, more preferably within the range of 1 to 10, still more preferably within the range of 1 to 6, and most preferably within the range of 1 to 4. Within such a range, it is preferable in that the curing reaction can proceed suitably.

The compound represented by the general formula (3) can be synthesized by reacting a compound which generates an active anion such as a malonic acid ester or an acetoacetic acid ester having an unsaturated bond in the molecule with an unsaturated compound having an alkyl ester group.

That is, malonic acid esters and acetoacetic acid have a methylene group interposed between carboxy carbons, and this methylene group is easily anionized and widely known as a group which readily produces anion reaction. A compound having an unsaturated bond in alkyl group of malonic acid ester or acetoacetic ester (for example, ester compounds of malonic acid or acetoacetic acid with an unsaturated monomer having a hydroxyl group as detailed below as a hydroxyl group-containing monomer) is reacted with an alkyl ester compound having an unsaturated group to synthesis a compound having both of an unsaturated group and an alkyl ester group.

Only the alkyl ester group in the compound having such a structure can be easily changed by using a raw material used widely, and as a result, the curing reactivity can be easily adjusted. In addition, it is particularly preferable in that the curing reactivity can be adjusted by changing the reaction ratio to an active methylene group.

The compound which can be used as the "alkyl ester compound having an unsaturated group" used in the above reaction is not particularly limited, and examples thereof include (meth) acrylic acid alkyl ester, methylene malonate alkyl ester, lactone compounds having an unsaturated group (for example, γ-crotonolactone, 5,6-dihydro-2H-pyran-2-one) and the like can be used.

The reaction can be carried out under basic conditions, and for example, can be carried out in an organic solvent in the presence of a crown ether of alkali metal salt. An example of such a synthesis reaction is shown below.

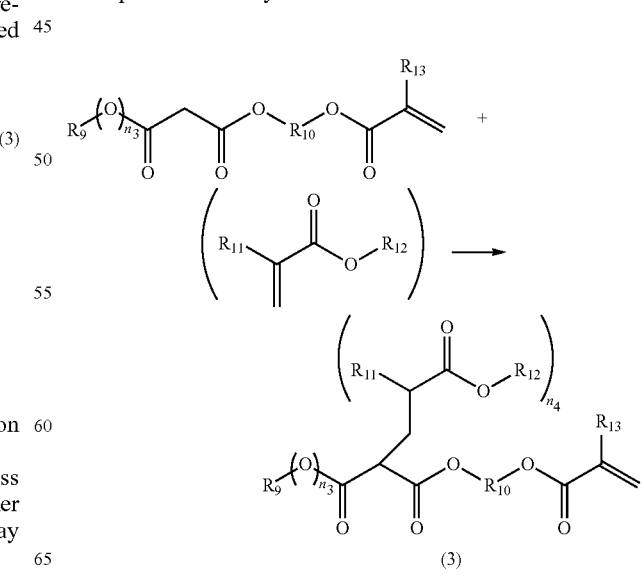

(3)

It can also be obtained by esterification of a carboxylic acid corresponding to the alkyl ester compound represented by the above general formula (1). That is, the compound represented by the following general formula (1-2) is a carboxylic acid corresponding to the alkyl ester compound represented by the general formula (1).

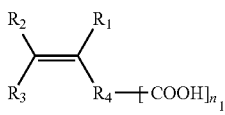

(1-2)

$n_1$: 1 to 10

(in the formula, $R_1$, $R_2$, and $R_3$ are the same or different, and each represents a hydrogen, an alkyl group, a carboxyl group, an alkyl ester group or a structure represented by the following $R_4$-[COOH]$n_1$;

$R_4$ is an aliphatic, an alicyclic or an aromatic alkylene group with a number of atoms of 50 or less in the main chain, which may have one or more functional groups selected from the group consisting of an ester group, an ether group, an amide group, and a urethane and may have a side chain.)

Known compounds exist as the compound represented by the general formula (1-2). Such known compounds can also be converted to unsaturated group-containing ester compounds of the present invention by carrying out a usual esterification reaction (for example, reaction with an alcohol corresponding to the alkyl group of the target alkyl ester).

Examples of specific chemical structures of compounds that can be synthesized by the methods exemplified above are shown below. It is to be noted that the present invention is not limited to the compounds exemplified below.

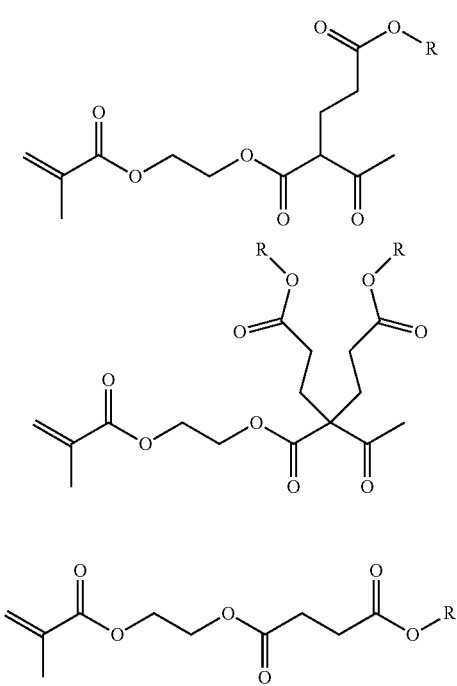

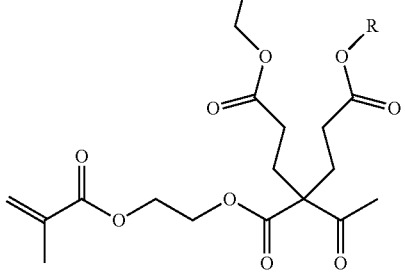

(In the above general formula, R represents an alkyl group.)

Also in the compound represented by the general formula, R in the general formula is an alkyl group having 50 or less carbon atoms, but the number of carbon atoms is preferably within the range of 1 to 20, more preferably within the range of 1 to 10, still more preferably within the range of 1 to 6, and most preferably within the range of 1 to 4. Within such a range, it is preferable in that the curing reaction can proceed suitably.

(Polymer)

The polymer (A) of the present invention is characterized by containing a structural unit derived from the unsaturated group-containing ester compound of the present invention described above in at least a portion thereof. That is, it is a homopolymer of the unsaturated group-containing ester compound of the present invention or a copolymer with other monomers.

As described above, the main object of the polymer (A) of the present invention is to use it as a component in a curable composition which undergoes a curing reaction by a transesterification reaction between an alkyl ester group and a hydroxyl group. In this case, the curable composition may contain a polymer having the hydroxyl group in the same polymer, or may contain a polymer using the alkyl ester group-containing monomer having no hydroxyl group, and contain a hydroxyl group-containing compound in combination. This point will be described later.

In the case where the polymer (A) used in the present invention is a copolymer, other monomers which can be used are described in detail below. Incidentally, a hydroxyl group-containing monomer can also be used as a copolymerization component, and the hydroxyl group-containing monomer and the polymer (C) using the same will be described later.

Various α-olefins such as ethylene, propylene, butadiene, or butane-1;

various halogenated olefins except fluoroolefin such as vinyl chloride or vinylidene chloride, various aromatic vinyl compounds such as styrene, α-methylstyrene or vinyltoluene;

various amino group-containing amide unsaturated monomers such as N-dimethylaminoethyl(meth)acrylamide, N-diethylaminoethyl(meth) acrylamide, N-dimethylaminopropyl(meth) acrylamide or N-diethylaminopropyl(meth) acrylamide;

various dialkylaminoalkyl(meth)acrylates such as dimethylaminoethyl(meth)acrylate or diethylaminoethyl(meth) acrylate;

various amino group-containing monomers such as tert-butylaminoethyl(meth) acrylate, tert-butylaminopropyl (meth)acrylate, aziridinyl ethyl(meth)acrylate, pyrrolidinylethyl(meth)acrylate or piperidinylethyl(meth)acrylate;

various carboxyl group-containing monomers such as (meth)acrylic acid, crotonic acid, itaconic acid, maleic acid or fumaric acid;

various epoxy group-containing monomers such as glycidyl (meth)acrylate, β-methylglycidyl(meth)acrylate or (meth) allyl glycidyl ether;

mono- or diesters of various α, β-unsaturated dicarboxylic acids such as maleic acid, fumaric acid or itaconic acid with monohydric alcohols having 1 to 18 carbon atoms;

various hydrolyzable silyl group-containing monomers such as vinyltrimethoxysilane, vinyltriethoxysilane, vinyltripropoxysilane, vinylmethyldiethoxysilane, vinyltris(β-methoxyethoxy) silane, allyltrimethoxysilane, trimethoxysilylethyl vinyl ether, triethoxysilylethyl vinyl ether, methyldimethoxysilyl ethyl vinyl ether, trimethoxysilylpropyl vinyl ether, triethoxysilylpropyl vinyl ether, methyldiethoxysilylpropyl vinyl ether, γ-(meth) acryloyloxypropyltrimethoxysilane, γ-(meth) acryloyloxypropyltriethoxysilane or γ-(meta) acryloyloxypropylmethyldimethoxysilane;

various fluorine-containing α-olefins such as vinyl fluoride, vinylidene fluoride, trifluoroethylene, tetrafluoroethylene, chlorotrifluoroethylene, bromotrifluoroethylene, pentafluoropropylene or hexafluoropropylene;

various fluorine atom-containing monomers such as various perfluoroalkyl perfluorovinyl ether or (per) fluoroalkyl vinyl ether (provided that the alkyl group has 1 to 18 carbon atoms) including trifluoro methyl trifluorovinyl ether, pentafluoroethyl trifluorovinyl ether or heptafluoropropyl trifluorovinyl ether;

various alkyl vinyl ethers or substituted alkyl vinyl ethers such as methyl vinyl ether, ethyl vinyl ether, n-propyl vinyl ether, isopropyl vinyl ether, n-butyl vinyl ether, isobutyl vinyl ether, tert-butyl vinyl ether, n-pentyl vinyl ether, n-hexyl vinyl ether, n-octyl vinyl ether, 2-ethylhexyl vinyl ether, chloromethyl vinyl ether, chloroethyl vinyl ether, benzyl vinyl ether or phenylethyl vinyl ether, various cycloalkyl vinyl ethers such as cyclopentyl vinyl ether, cyclohexyl vinyl ether or methyl cyclohexyl vinyl ether;

various aliphatic carboxylic acid vinyls such as vinyl 2,2-dimethyl propanoate, vinyl 2,2-dimethyl butanoate, vinyl 2,2-dimethyl pentanoate, vinyl 2,2-dimethyl hexanoate, vinyl 2-ethyl-2-methyl butanoate, vinyl 2-ethyl-2-methyl pentanoate, vinyl 3-chloro-2,2-dimethyl propanoate and the like, as well as vinyl acetate, vinyl propionate, vinyl butyrate, vinyl isobutyrate, vinyl caproate, vinyl caprylate, vinyl caprate or vinyl laurate, C9 branched aliphatic carboxylic acid vinyl, C10 branched aliphatic carboxylic acid vinyl, C11 branched aliphatic carboxylic acid vinyl or vinyl stearate;

vinyl esters of carboxylic acids having a cyclic structure such as vinyl cyclohexane carboxylate, vinyl methyl cyclohexane carboxylate, vinyl benzoate or vinyl p-tert-butylbenzoate.

In the above polymer (A), one obtained by using an unsaturated group-containing ester compound other than the unsaturated group-containing ester compound of the present invention represented by the general formula (1) as a part of the monomer may be used. Such other unsaturated group-containing ester compound is not particularly limited, and examples thereof include methyl(meth) acrylate, ethyl (meth) acrylate, n-propyl(meth) acrylate, benzyl(meth) acrylate, isopropyl(meth) acrylate, n-butyl(meth) acrylate, isobutyl(meth) acrylate, sec-butyl(meth) acrylate, t-butyl (meth) acrylate and the like.

In the polymer (A), a polymer can be obtained by combining the above-mentioned various monomers as necessary and polymerizing in accordance with a known method. The polymer (A) preferably contain the unsaturated group-containing ester compound of the present invention as a constituting unit at a ratio of 1 to 100% by weight of. The lower limit of the content ratio is more preferably 10% by weight, and still more preferably 20% by weight. By setting the amount within this range, a thermosetting resin composition having a good curing performance can be obtained.

The method for producing the polymer (A) is not particularly limited, and the polymer (A) can be produced by polymerization by a known method. More specifically, polymerization methods such as a solution polymerization method in an organic solvent, an emulsion polymerization method in water, a miniemulsion polymerization method in water, an aqueous solution polymerization method, a suspension polymerization method, a UV curing method, an anionic polymerization, and a cationic polymerization can be mentioned.

Further, a water-borne one obtained by dispersing in water after solution polymerization in an organic solvent is carried out, or one obtained by dissolving a resin which polymerized in water in an organic solvent, may be used.

In the present invention, the polymer (A) preferably has a weight average molecular weight of 3,000 to 300,000. The upper limit of the weight average molecular weight of the polymer is more preferably 100,000, further preferably 50,000, and still more preferably 30,000. The lower limit of the weight average molecular weight of the above component (X) is more preferably 3,000, and still more preferably 5,000.

(Thermosetting Resin Composition)

In the present invention, a thermosetting resin composition can be obtained using the above-mentioned polymer (A) as an essential component. In the thermosetting resin composition of the present invention, it is necessary for the hydroxyl group to be present in the composition, and it is also essential to incorporate a transesterification catalyst.

When a thermosetting resin composition is obtained using the polymer of the present invention, it is necessary that an alkyl ester group and a hydroxyl group are present in the system. A method to obtain such a system in which both an alkyl ester group and a hydroxyl group are present is mentioned below;

(I) a polymer (C) having an alkyl ester group and a hydroxyl group, (II) a composition containing an alkyl ester group-containing polymer (D) having no hydroxyl group and a hydroxyl group-containing compound (E)

(III) a composition containing a polymer (C) having an alkyl ester group and a hydroxyl group, an alkyl ester group-containing polymer (D) having no hydroxyl group and a hydroxyl group-containing compound (E) Either method may be used.

The polymer (A) of the present invention may correspond to any of the above (I) to (III). That is, in order to make it correspond to (I) (III), the polymer (A) may be a polymer (C) having a hydroxyl group, and in order to make it correspond to (II) (III), the polymer (A) may be a polymer (D) having no hydroxyl group.

The alkyl ester group-containing polymer (D) having no hydroxyl group is a polymer containing the above-mentioned unsaturated group-containing ester compound of the present invention as a part or all of its constituent units. Such a polymer is as described above.

In the thermosetting resin composition, in the case of the polymer (C) to be used in the embodiment of the above (I)

(III), in the production of the polymer of the present invention, a hydroxyl group-containing monomer is used.

The hydroxyl group-containing monomer that can be used in the polymer (C) having an alkyl ester group and a hydroxyl group is not particularly limited, and the following can be exemplified.

Various hydroxyl group-containing vinyl ethers such as 2-hydroxyethyl vinyl ether, 3-hydroxypropyl vinyl ether, 2-hydroxypropyl vinyl ether, 4-hydroxybutyl vinyl ether, 3-hydroxybutyl vinyl ether, 2-hydroxy-2-methylpropyl vinyl ether, 5-hydroxypentyl vinyl ether or 6-hydroxyhexyl vinyl ether;
addition reaction products of these various vinyl ethers and ε-caprolactone; various hydroxyl group-containing (meth) allyl ethers such as 2-hydroxyethyl(meth)allyl ether, 3-hydroxypropyl(meth)allyl ether, 2-hydroxypropyl(meth)allyl ether, 4-hydroxybutyl(meth)allyl ether, 3-hydroxybutyl (meth)allyl ether, 2-hydroxy-2-methylpropyl(meth)allyl ether, 5-hydroxypentyl(meth)allyl ether or 6-hydroxyhexyl (meth)allyl ether; addition reaction products of these various allyl ethers and ε-caprolactone;

various hydroxyl group-containing (meth)acrylates such as 2-hydroxyethyl(meth)acrylate, 2-hydroxypropyl(meth) acrylate, 3-hydroxypropyl(meth)acrylate, 2-hydroxybutyl (meth) acrylate, 3-hydroxybutyl(meth) acrylate, 4-hydroxybutyl(meth)acrylate, polyethylene glycol mono(meth) acrylate or polypropylene glycol mono(meth)acrylate; or main components of addition reaction of these various (meth) acrylates and ε-caprolactone.

In addition, the hydroxyl group-containing monomer as a monomer does not have a hydroxyl group at a position close to the unsaturated bond (specifically, the number of atoms between the hydroxyl group and the unsaturated bond is 2 or less). In the case of having a hydroxyl group via a connecting chain having an atomic number of 3 to 50, the hydroxyl group becomes easy to move in the resin, so that it is preferable from the viewpoint that the transesterification easily occurs.

That is, when the hydroxyl group-containing monomer has a hydroxyl group via a connecting chain having an atomic number of 3 to 50, it has both this structure and a structure derived from the unsaturated group-containing ester compound of the present invention so that it will be possible to obtain unprecedented curing performance at low temperature of 80° C. In view of obtaining such an unexpected effect, it is preferable to use the above-mentioned hydroxyl group-containing monomer. Such an effect is presumed to be obtained because both of the alkyl ester group and the hydroxyl group become in a state of high degree of freedom in the resin, so that the transesterification reaction tends to occur.

More specifically, it is preferable to use a hydroxyl group-containing monomer having a structure represented by the following general formula (4) for a part or all of the hydroxyl groups.

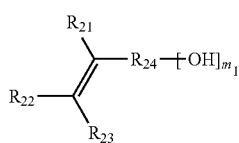

(4)

$m_1$: 1 to 10
(in the formula, $R_{21}$, $R_{22}$, and $R_{23}$ are the same or different, and each represents a hydrogen, an alkyl group, a carboxyl group, an alkyl ester group or a structure represented by the following $R_{24}$-$[OH]_{m_1}$;
$R_{24}$ is an aliphatic, an alicyclic or an aromatic alkylene group with a number of atoms of 3 to 50 in the main chain, which may have one or more functional groups selected from the group consisting of an ester group, an ether group, an amide group, and a urethane and may have a side chain.)

In addition, the compound represented by the above general formula (4) is preferably a derivative of (meth) acrylic acid represented by the following general formula (5).

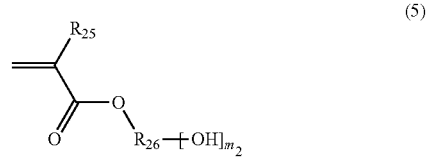

(5)

$m_2$: 1 to 10
($R_{25}$ is H or $CH_3$; and $R_{26}$ is an aliphatic, an alicyclic or an aromatic alkylene group with a number of atoms of 3 to 49 in the main chain, which may have one or more functional groups selected from the group consisting of an ester group, an ether group, an amide group, and a urethane and may have a side chain.)

Specific examples of such a compound having a hydroxyl group via a connecting chain having a molecular number of 3 to 50 in the main chain include (meth)acrylates such as 3-hydroxypropyl(meth)acrylate, 4-hydroxybutyl(meth) acrylate, 1,4-cyclohexane dimethanol mono(meth)acrylate, polyethylene glycol mono(meth)acrylate and polypropylene glycol mono(meth)acrylate, and various addition reaction main components of the above-mentioned (meth)acrylates with ε-caprolactone the like.

The polymer (C) having a structural unit having the hydroxyl group-containing monomer can also be polymerized by the same method as the above-mentioned polymer (A).

When the thermosetting resin composition of the present invention is in any one embodiment of the following (II) and (III),
(II) a composition containing an alkyl ester group-containing polymer (D) having no hydroxyl group and a hydroxyl group-containing compound (E)
(III) a composition containing a polymer (C) having an alkyl ester group and a hydroxyl group, an alkyl ester group-containing polymer (D) having no hydroxyl group and a hydroxyl group-containing compound (E),
the hydroxyl group-containing compound (E) is used. Such a hydroxyl group-containing compound (E) is not particularly limited, and it may be a resin or a low molecular weight compound.

Hereinafter, the compounds that can be used as such hydroxyl group-containing compound (E) will be described in detail.
Polymer of Unsaturated Monomer Having Hydroxyl Group (E-1)

Such a polymer can be produced, for example, by copolymerizing a hydroxyl group-containing polymerizable unsaturated monomer and another polymerizable unsaturated monomer copolymerizable therewith by a known method. More specifically, there can be mentioned a polymerization method such as a solution polymerization method in an organic solvent, an emulsion polymerization method in water, a miniemulsion polymerization method in water, an aqueous solution polymerization method, or the like.

The hydroxyl group-containing polymerizable unsaturated monomer is a compound having one or more hydroxyl groups and polymerizable unsaturated bonds in one molecule. As the hydroxyl group-containing polymerizable unsaturated monomer, the same hydroxyl group-containing monomer that can be used in the above-mentioned polymer (C) can be used.

Also in the polymer (E-1) of unsaturated monomer having a hydroxyl group, when the monomer represented by the above general formula (4) or (5) is used as a hydroxyl group-containing monomer in part or in whole, the curing reactivity is good, and a curing reaction at 80° C. can be caused, which is preferable.

Examples of the other polymerizable unsaturated monomer copolymerizable with the hydroxyl group-containing monomer include the following monomers (i) to (xiv), and the like, and any combination thereof.

(i) Alkyl or cycloalkyl(meth)acrylate:
methyl(meth)acrylate, ethyl(meth)acrylate, n-propyl(meth)acrylate, isopropyl(meth)acrylate, n-butyl(meth) acrylate, isobutyl(meth) acrylate, tert-butyl(meth)acrylate, n-hexyl (meth)acrylate, n-octyl(meth)acrylate, 2-ethylhexyl(meth)acrylate, nonyl(meth)acrylate, tridecyl(meth)acrylate, lauryl (meth)acrylate, stearyl(meth)acrylate, isostearyl(meth) acrylate, cyclohexyl(meth) acrylate, methylcyclohexyl (meth) acrylate, tert-butylcyclohexyl(meth) acrylate, cyclododecyl(meth) acrylate, tricyclodecanyl(meth) acrylate, etc.

(ii) Polymerizable unsaturated monomer having an isobornyl group: isobornyl(meth)acrylate, etc.

(iii) Polymerizable unsaturated monomer having an adamantyl group: adamantyl(meth)acrylate, etc.

(iv) Polymerizable unsaturated monomer having a tricyclodecenyl group: tricyclodecenyl(meth) acrylate, etc.

(v) Aromatic ring-containing polymerizable unsaturated monomer: benzyl(meth)acrylate, styrene, α-methylstyrene, vinyltoluene, etc.

(vi) Polymerizable unsaturated monomer having an alkoxysilyl group:
vinyltrimethoxysilane, vinyltriethoxysilane, vinyltris(2-methoxyethoxy) silane, γ-(meth) acryloyloxypropyltrimethoxysilane, γ-(meth) acryloyloxypropyltriethoxysilane, etc.

(vii) Polymerizable unsaturated monomer having a fluorinated alkyl group: perfluoroalkyl(meth)acrylates such as perfluorobutyl ethyl(meth)acrylate and perfluorooctylethyl (meth) acrylate; fluoroolefins, etc.

(viii) Polymerizable unsaturated monomer having a photopolymerizable functional group such as a maleimide group.

(iv) Vinyl compound: N-vinyl pyrrolidone, ethylene, butadiene, chloroprene, vinyl propionate, vinyl acetate etc.

(x) Carboxyl group-containing polymerizable unsaturated monomer: (meth)acrylic acid, maleic acid, crotonic acid, β-carboxyethyl acrylate, etc.

(xi) Nitrogen-containing polymerizable unsaturated monomer: (meth)acrylonitrile, (meth)acrylamide, N, N-dimethylaminoethyl(meth) acrylate, N, N-diethylaminoethyl(meth) acrylate, N, N-dimethylaminopropyl(meth) acrylamide, methylene bis(meth)acrylamide, ethylenebis(meth)acrylamide, adducts of glycidyl(meth)acrylate and an amine compound, etc.

(xii) Polymerizable unsaturated monomer having two or more polymerizable unsaturated groups in one molecule: allyl(meth)acrylate, 1,6-hexanediol di(meth)acrylate, etc.

(xiii) Epoxy group-containing polymerizable unsaturated monomer: glycidyl(meth) acrylate, β-methylglycidyl(meth) acrylate, 3,4-epoxycyclohexylmethyl(meth) acrylate, 3,4-epoxycyclohexylethyl(meth) acrylate, 3,4-epoxycyclohexylpropyl(meth)acrylate, allyl glycidyl ether, etc.

(xiv) (Meth)acrylate having a polyoxyethylene chain whose molecular terminal is an alkoxy group:

(xv) Polymerizable unsaturated monomer having a sulfonic acid group: 2-acrylamido-2-methylpropanesulfonic acid, 2-sulfoethyl(meth)acrylate, allylsulfonic acid, 4-styrenesulfonic acid and the like; sodium salts and ammonium salts etc. of these sulfonic acids.

(xvi) Polymerizable unsaturated monomer having a phosphoric acid group: acid phosphoxyethyl(meth)acrylate, acid phosphoxypropyl(meth) acrylate, acid phosphoxy poly(oxyethylene)glycol (meth)acrylate, acid phosphoxy poly(oxypropylene)glycol (meth) acrylate, etc.

(xvii) Polymerizable unsaturated monomer having an ultraviolet absorbing functional group: 2-hydroxy-4-(3-methacryloyloxy-2-hydroxypropoxy)benzophenone, 2-hydroxy-4-(3-acryloyloxy-2-hydroxypropoxy)benzophenone, 2,2'-dihydroxy-4-(3-methacryloyloxy-2-hydroxypropoxy) benzophenone, 2,2'-dihydroxy-4-(3-acryloyloxy-2-hydroxypropoxy)benzophenone, 2-(2'-hydroxy-5'-methacryloyloxyethylphenyl)-2H-benzotriazole, etc.

(xviii) Ultraviolet stable polymerizable unsaturated monomer: 4-(meth)acryloyloxy-1,2,2,6,6-pentamethylpiperidine, 4-(meth)acryloyloxy-2,2,6,6-tetramethylpiperidine, 4-cyano-4-(meth)acryloylamino-2,2,6,6-tetramethylpiperidine, 1-(meth)acryloyl-4-(meth)acryloylamino-2,2,6,6-tetramethylpiperidine, 1-(meth)acryloyl-4-cyano-4-(meth) acryloylamino-2,2,6,6-tetramethylpiperidine, 4-crotonoyloxy-2,2,6,6-tetramethylpiperidine, 4-crotonoylamino-2,2,6,6-tetramethylpiperidine, 1-crotonoyl-4-crotonoyloxy-2,2,6,6-tetramethylpiperidine and the like.

(xiv) Polymerizable unsaturated monomer having a carbonyl group: acrolein, diacetone acrylamide, diacetone methacrylamide, acetoacetoxyethyl methacrylate, formylstyrene, vinyl alkyl ketone having about 4 to about 7 carbon atoms (for example, vinyl methyl ketone, vinyl ethyl ketone, vinyl butyl ketone), and etc.

In the present specification, "polymerizable unsaturated group" means an unsaturated group capable of radical polymerization or ionic polymerization. Examples of the polymerizable unsaturated group include a vinyl group and a (meth)acryloyl group.

The proportion of the hydroxyl group-containing monomer in preparing the polymer (E-1) of unsaturated monomer having a hydroxyl group is preferably 0.5 to 50% by weight based on the total amount of the monomer components. Within such a range, an appropriate crosslinking reaction can be caused, and excellent coating film physical properties can be obtained.

The lower limit is more preferably 1.0% by weight, and still more preferably 1.5% by weight. The upper limit is more preferably 40% by weight.

The hydroxyl value of the polymer (E-1) of unsaturated monomer having a hydroxyl group is preferably 1 to 200 mg KOH/g from the viewpoint of water resistance of the formed coating film and the like. The lower limit is more preferably 2 mg KOH/g, and still more preferably 5 mg KOH/g. The upper limit is more preferably 180 mg KOH/g, and still more preferably 170 mg KOH/g.

As the polymer (E-1) of unsaturated monomer having a hydroxyl group, commercially available one can also be used. Commercial ones are not particularly limited, and for example, ACRYDIC A-801-P, A-817, A-837, A-848-RN, A-814, 57-773, A-829, 55-129, 49-394-IM, A-875-55, A-870, A-871, A-859-B, 52-668-BA, WZU-591, WXU-880, BL-616, CL-1000, CL-408, and the like manufactured by DIC Corporation.

In the thermosetting coating of the present invention, the alkyl ester group is preferably 1 to 200% (number ratio) relative to the number of hydroxyl groups derived from the polymer (E-1) of unsaturated monomer having a hydroxyl group when the ester group is a tertiary ester, although it can be blended arbitrarily.

Polyester Polyol (E-2)

The polyester polyol (E-2) can usually be produced by an esterification reaction or a transesterification reaction of an acid component and an alcohol component. As the above-mentioned acid component, a compound which is ordinarily used as an acid component in the production of a polyester resin can be mentioned. Examples of the acid component include aliphatic polybasic acids, alicyclic polybasic acids, aromatic polybasic acids and the like, and anhydrides and esterified products thereof.

As the above aliphatic polybasic acid, and anhydride and esterified product thereof, aliphatic compounds having two or more carboxyl groups in one molecule, an acid anhydride of the aliphatic compound and an esterified product of the aliphatic compound are generally mentioned, for example, aliphatic polyvalent carboxylic acids such as succinic acid, glutaric acid, adipic acid, pimelic acid, suberic acid, azelaic acid, sebacic acid, undecane diacid, dodecanedioic acid, brassylic acid, octadecanedioic acid, citric acid, and butanetetracarboxylic acid; anhydrides of the above aliphatic polyvalent carboxylic acids; esterified products of lower alkyl having about 1 to about 4 carbon atoms of the aliphatic polyvalent carboxylic acid, and the like, and any combinations thereof may be mentioned.

The aliphatic polybasic acid is preferably adipic acid and/or adipic anhydride from the viewpoint of the smoothness of the coating film to be obtained.

The above-mentioned alicyclic polybasic acids, and their anhydrides and esterified products are generally compounds having one or more alicyclic structures and two or more carboxyl groups in one molecule, acid anhydrides of the above compounds and esterified products of the above compounds. The alicyclic structure is mainly a 4- to 6-membered ring structure. Examples of the alicyclic polybasic acid and anhydride and esterified product thereof include the alicyclic polyvalent carboxylic acids such as 1,2-cyclohexanedicarboxylic acid, 1,3-cyclohexanedicarboxylic acid, 1,4-cyclohexanedicarboxylic acid, 4-cyclohexene-1, 2-dicarboxylic acid, 3-methyl-1,2-cyclohexanedicarboxylic acid, 4-methyl-1,2-cyclohexanedicarboxylic acid, 1,2,4-cyclohexanetricarboxylic acid, 1,3,5-cyclohexanetricarboxylic acid and the like; anhydrides of the alicyclic polyvalent carboxylic acids; esterified products of the lower alkyl having about 1 to about 4 carbon atoms of the alicyclic polyvalent carboxylic acid, and the like; and any combinations thereof may be mentioned.

From the viewpoint of the smoothness of the coating film to be obtained, it is preferable to use 1,2-cyclohexanedicarboxylic acid, 1,2-cyclohexanedicarboxylic anhydride, 1,3-cyclohexanedicarboxylic acid, 1,4-cyclohexanedicarboxylic acid, 4-cyclohexene-1,2-dicarboxylic acid and 4-cyclohex-ene-1,2-dicarboxylic anhydride, and 1,2-cyclohexane dicarboxylic acid and/or 1,2-cyclohexanedicarboxylic anhydride is more preferable.

The above aromatic polybasic acid and their anhydride and esterified product may generally include aromatic polyvalent carboxylic acids such as an aromatic compound having two or more carboxyl groups in one molecule, an acid anhydride of the aromatic compound and an esterified product of the aromatic compound including phthalic acid, isophthalic acid, terephthalic acid, naphthalene dicarboxylic acid, 4,4'-biphenyl dicarboxylic acid, trimellitic acid, pyromellitic acid and the like; acid anhydride of the aromatic polyvalent carboxylic acid, esterified products of lower alkyl having about 1 to about 4 carbon atoms of the aromatic polyvalent carboxylic acid, and the like, and any combinations thereof. As the above aromatic polybasic acid and their anhydride and esterified product, phthalic acid, phthalic anhydride, isophthalic acid, trimellitic acid, and trimellitic anhydride are preferable.

Further, as the acid component, acid components other than the aliphatic polybasic acid, the alicyclic polybasic acid and the aromatic polybasic acid, for example, fatty acids such as coconut oil fatty acid, cottonseed oil fatty acid, hemp oil fatty acid, rice bran oil fatty acid, fish oil fatty acid, Tall oil fatty acid, soybean oil fatty acid, linseed oil fatty acid, tung oil fatty acid, rapeseed oil fatty acid, castor oil fatty acid, dehydrated castor oil fatty acid, safflower oil fatty acid etc.; monocarboxylic acids such as lauric acid, myristic acid, palmitic acid, stearic acid, oleic acid acid, linoleic acid, linolenic acid, benzoic acid, p-tert-butylbenzoic acid, cyclohexanoic acid, 10-phenyloctadecanoic acid and the like; hydroxy carboxylic acids such as lactic acid, 3-hydroxybutanoic acid, 3-hydroxy-4-ethoxybenzoic acid, and the like, and any combination thereof may be mentioned.

As the alcohol component, a polyhydric alcohol having two or more hydroxyl groups in one molecule may be used. The polyhydric alcohol may include, for example, dihydric alcohols such as ethylene glycol, propylene glycol, diethylene glycol, trimethylene glycol, tetraethylene glycol, triethylene glycol, dipropylene glycol, 1,4-butanediol, 1,3-butanediol, 2,3-butanediol, 1,2-butane diol, 2-methyl-1,3-propanediol, 3-methyl-1,2-butanediol, 1,1,1-trimethylolpropane, 2-butyl-2-ethyl-1,3-propanediol, 1,2-pentanediol, 1,5-pentanediol, 1,4-pentanediol, 2,4-pentanediol, 2,3-dimethyltrimethylene glycol, tetramethylene glycol, 3-methyl-4,3-pentanediol, 3-methyl-1,5-pentanediol, 2,2,4-trimethyl-1,3-pentanediol, 1,6-hexanediol, 1,5-hexanediol, 1,4-hexanediol, 2,5-hexanediol, neopentyl glycol, 1,4-cyclohexanedimethanol, tricyclodecanedimethanol, hydroxypivalic acid neopentyl glycol ester, hydrogenated bisphenol A, hydrogenated bisphenol F, and dimethylolpropionic acid; polylactone diol obtained by adding a lactone compound such as ε-caprolactone to the dihydric alcohol; ester diol compounds such as bis(hydroxyethyl) terephthalate; polyether diol compounds such as alkylene oxide adducts of bisphenol A, polyethylene glycol, polypropylene glycol and polybutylene glycol; trihydric or higher alcohol such as glycerin, trimethylolethane, trimethylolpropane, diglycerin, triglycerin, 1,2,6-hexanetriol, pentaerythritol, dipentaerythritol, tris(2-hydroxyethyl) isocyanuric acid, sorbitol, and mannitol; a polylactone polyol compound obtained by adding a lactone compound such as ε-caprolactone to the trihydric or higher alcohol; fatty acid esterified products of glycerin, and the like.

As the above-mentioned alcohol component, an alcohol component other than the polyhydric alcohol, for example, a monoalcohol such as methanol, ethanol, propyl alcohol, butyl alcohol, stearyl alcohol or 2-phenoxyethanol; and an alcohol compound obtained by reacting a monoepoxy compound such as propylene oxide, butylene oxide, "Cardura E10" (trade name, glycidyl esters of synthetic hyperbranched saturated fatty acids, manufactured by HEXION Specialty Chemicals, Inc.) with an acid may be used.

The polyester polyol (E-2) is not particularly limited, and it can be produced by a usual method. For example, the acid component and the alcohol component are heated in a nitrogen stream at about 150 to about 250° C. for about 5 to about 10 hours to carry out esterification reaction or transesterification reaction of the acid component and the alcohol component, thereby the polyester polyol (E-2) can be produced.

The Low Molecular Weight Polyol (E-3)

The above compound (E) is not limited to the abovementioned resin, and a low molecular weight polyol (specifically, molecular weight of 2,000 or less) can also be used. As the low molecular weight polyol, for example, dihydric alcohols such as ethylene glycol, propylene glycol, diethylene glycol, trimethylene glycol, tetraethylene glycol, triethylene glycol, dipropylene glycol, 1,4-butanediol, 1,3-butanediol, 2,3-butanediol, 1,2-butane diol, 2-methyl-1,3-propanediol, 3-methyl-1,2-butanediol, 2-butyl-2-ethyl-1,3-propanediol, 1,2-pentanediol, 1,5-pentanediol, 1,4-pentanediol, 2,4-pentanediol, 2,3-dimethyltrimethylene glycol, tetramethylene glycol, 3-methyl-4,3-pentanediol, 3-methyl-1,5-pentanediol, 2,2,4-trimethyl-1,3-pentanediol, 1,6-hexanediol, 1,5-hexanediol, 1,4-hexanediol, 2,5-hexanediol, neopentyl glycol, 1,4-cyclohexanedimethanol, tricyclodecanedimethanol, hydroxypivalic acid neopentyl glycol ester, hydrogenated bisphenol A, hydrogenated bisphenol F, and dimethylolpropionic acid; polylactone diol obtained by adding a lactone compound such as ε-caprolactone to the dihydric alcohol; ester diol compounds such as bis(hydroxyethyl) terephthalate; polyether diol compounds such as alkylene oxide adducts of bisphenol A, polyethylene glycol, polypropylene glycol and polybutylene glycol; trihydric or higher alcohol such as glycerin, trimethylolethane, trimethylolpropane, diglycerin, triglycerin, 1,2,6-hexanetriol, pentaerythritol, dipentaerythritol, tris(2-hydroxyethyl) isocyanuric acid, sorbitol, and mannitol.

As for the thermosetting resin composition using such a low molecular weight polyol, the low molecular weight polyol to be used is known as a general purpose product and can be obtained at low cost. Further, the low molecular weight polyol has high water solubility and can be suitably used as a crosslinking agent in the case of curing in water-borne system. In recent years, environmental problems are attracting attention, and it can be suitably used as a very important crosslinking agent in promoting the reduction of VOC.

As the compound (E) of the present invention, two or more of the polyacrylic polyol (E-1), the polyester polyol (E-2) and the low molecular weight polyol (E-3) may be used in combination.

In the thermosetting coating of the present invention, the alkyl ester group is preferably 1 to 200% (number ratio) relative to the number of hydroxyl groups in the whole composition when the ester group is a tertiary ester, although it can be blended arbitrarily.

(Transesterification Catalyst (F))

The thermosetting resin composition of the present invention contains a transesterification catalyst (F). That is, the transesterification catalyst (F) is added to generate a transesterification reaction between the ester group and the hydroxyl group efficiently and obtain sufficient thermosetting property.

As the transesterification catalyst (F), any known compound capable of activating the transesterification reaction can be used.

Specifically, it may include, for example, various acidic compounds such as hydrochloric acid, sulfuric acid, nitric acid, acetic acid, phosphoric acid or sulfonic acid and the like; various basic compounds such as LiOH, KOH or NaOH, amines and the like; and various metal compounds such as PbO, zinc acetate, lead acetate, antimony trioxide, tetraisopropyl titanate, dibutyl tin dilaurate, dibutyl tin dioctate or monobutyl stannate, and the like. It is also possible to use a photoresponsive catalyst or a thermal latent catalyst which generates acid by light or heat.

Among them, as a material which can sufficiently exhibit the effect of the present invention, it is preferable to use a compound having a sulfonic acid group (dodecylbenzenesulfonic acid, phenolsulfonic acid, metasulfonic acid, paratoluenesulfonic acid) or a compound having a group consisting of an alkali metal salt, or an amine salt of sulfonic acid.

It is also possible to suitably use metal compounds including tin compounds such as dibutyltin dilaurate, dibutyltin dioctate, dibutyltin oxide and monobutyl stannate, and aluminum compounds such as aluminum alkylacetoacetate diisopropylate, aluminum monoacetylacetonate bis (ethylacetoacetate), tris(alkylacetoacetate) aluminum, aluminum acetylacetonate as the transesterification catalyst (F).

Since the tin compound and the aluminum compound have high catalytic activity, a thermosetting resin composition having high curing reactivity can be obtained. In addition, it is preferable in that, even when a resin having a primary alkyl ester group or a secondary alkyl ester group having a relatively low reactivity is used, it can be cured very efficiently.

The amount of the transesterification catalyst (F) used is preferably 0.01 to 50% by weight based on the total weight of the polymer. Within such a range, it is preferable in that good curing reaction can be carried out at low temperature.

The form of the thermosetting resin composition of the present invention is not particularly limited, but it is particularly preferably an organic solvent-type form or a waterborne form. This is preferable in that thin film coating can be performed and low-temperature curing can be performed. The water-borne system may be water-soluble or waterdispersible, and it may contain an aqueous solvent that can be mixed with water at an arbitrary ratio such as ethanol, methanol, alcohol type, glycol type, ether type, ketone type or the like in addition to water.

The organic solvent-type thermosetting resin composition is a composition in which the above components are dissolved or dispersed in various organic solvents. The organic solvent that can be used is not particularly limited, and examples thereof include hydrocarbons such as 1-hexane, 1-octane, 1-decane, 1-tetradecane, cyclohexane, benzene and xylene, ethers such as dimethyl ether and diethyl ether, ketones such as acetone, and methyl ethyl ketone, chlorinated hydrocarbons such as trichloromethane, carbon tetrachloride, dichloroethane, trichloroethane, tetrachloroethylene and the like, and any known ones such as ethanol, methanol, propanol, butanol, acetone, cyclohexanone and the like.

Further, as a two-component resin composition, a solution containing the ester compound and a solution containing the hydroxyl group-containing compound may be combined and mixed immediately before use. It is preferable in that storage stability is good. It is also possible to use a two-component type in which a catalyst solution containing the transesterification catalyst (F) is mixed with a solution containing the composition having the alkyl ester group and the hydroxyl group.

Further, in the case of preparing a powdery thermosetting resin composition such as a powder coating, it can be prepared by drying, mixing, and crushing each of the above-mentioned components according to a usual way.

The thermosetting resin composition of the present invention may further be used in combination with other crosslinking agents commonly used in the fields of coatings and adhesives in addition to the above components (A) to (C). The crosslinking agent that can be used is not particularly limited, and examples thereof include an isocyanate compound, a blocked isocyanate compound, a melamine resin, an epoxy resin, a silane compound, and the like. In addition, vinyl ether, an anionic polymerizable monomer, a cationic polymerizable monomer, and a radical polymerizable monomer, etc. may be used in combination. A curing agent for accelerating the reaction of the used crosslinking agent may be used in combination.

The thermosetting resin composition of the present invention can be suitably used in the fields of thermosetting coatings, thermosetting adhesives and the like.

When it is used as a thermosetting coating material, in addition to each of the above-described components, additives commonly used in the coating material field may be used in combination. For example, coloring pigments, extender pigments, bright pigments and the like, and any combination thereof may be used in combination.

When a pigment is used, it is preferably contained in a total amount of 1 to 500% by weight, based on 100% by weight of the total solid content of the resin component. The lower limit is more preferably 3% by weight, and still more preferably 5 parts by weight. The upper limit is more preferably 400% by weight, and still more preferably 300% by weight.

Examples of the coloring pigment include titanium oxide, zinc white, carbon black, molybdenum red, prussian blue, cobalt blue, azo pigment, phthalocyanine pigment, quinacridone pigment, isoindoline pigment, threne pigment, perylene pigment, dioxazine type pigment, diketopyrrolopyrrole type pigment, and the like, and any combination thereof.

Examples of the extender pigment include clay, kaolin, barium sulfate, barium carbonate, calcium carbonate, talc, silica, alumina white and the like, and barium sulfate and/or talc is preferable, and barium sulfate is more preferable.

Examples of the bright pigment include, for example, aluminum oxide coated with aluminum (including vapor-deposited aluminum), copper, zinc, brass, nickel, aluminum oxide, mica, titanium oxide or iron oxide, mica coated with titanium oxide or iron oxide, glass flakes, hologram pigments, etc., and any combinations thereof. The aluminum pigment includes nonleafing type aluminum and leafing type aluminum.

If desired, the thermosetting coating may further contain an additive for coating such as a thickener, an ultraviolet absorber, a light stabilizer, an antifoaming agent, a plasticizer, an organic solvent other than the hydrophobic solvent, a surface conditioner, an anti-settling agent, and the like.

Examples of the thickener include inorganic thickeners such as silicate, metal silicate, montmorillonite, colloidal alumina and the like; polyacrylic acid thickeners such as copolymers of (meth)acrylic acid and (meth)acrylic acid ester, and sodium polyacrylate; associative type thickener having a hydrophilic part and a hydrophobic part in one molecule and showing a thickening effect by an adsorption of the hydrophobic portion on the surface of the pigment or emulsion particle in the coating, or an association of the hydrophobic parts, in an aqueous medium; cellulose derivative thickeners such as carboxymethylcellulose, methylcellulose, hydroxyethylcellulose and the like; protein type thickeners such as casein, sodium caseinate, ammonium caseinate and the like alginic acid thickeners such as sodium alginate; polyvinyl thickeners such as polyvinyl alcohol, polyvinyl pyrrolidone, polyvinyl benzyl ether copolymers; polyether thickeners such as pluronic polyethers, polyether dialkyl esters, polyether dialkyl ethers, polyether epoxy modified products and the like; maleic anhydride copolymer type thickener such as a partial ester of vinyl methyl ether-maleic anhydride copolymer; polyamide type thickeners such as a polyamide amine salt, etc., and any combination thereof.

The polyacrylic acid thickener is commercially available, and examples thereof include "ACRYSOLASE-60", "ACRYSOLTT-615", and "ACRYSOLRM-5" (trade names) manufactured by Rohm and Haas Company, and "SN Thickener 613", "SN Thickener 618", "SN Thickener 630", "SN Thickener 634", and "SN Thickener 636" (trade names) manufactured by San Nopco CO., LTD.

The associative type thickener is commercially available, and examples thereof include "UH-420", "UH-450", "UH-462", "UH-472", "UH-540", "UH-752", "UH-756VF", and "UH-814N" (trade names) manufactured by ADEKA Corporation, "ACRYSOLRM-8W", "ACRYSOLRM-825", "ACRYSOLRM-2020NPR", "ACRYSOLRM-12W", and "ACRYSOLSCT-275" (trade names) manufactured by Rohm and Haas Company, "SN Thickner 612", "SN Thickener 621 N", "SN Thickener 625 N", "SN Thickener 627 N", and "SN Thickener 660 T" (trade names) manufactured by SAN NOPCO CO., LTD. and the like.

The object to which the thermosetting coating can be applied is not particularly limited, and examples thereof include an outer plate portion of an automobile body such as a passenger car, a truck, a motorcycle, and a bus; an automobile part; house electrical products such as a mobile phone, an audio device, etc., building materials, furniture, adhesives, film and glass coating agents, and the like. When used as an automotive coating, it can be used for the effect of an arbitrary layer such as an intermediate coating, a base coating and a clear coating.

The object to be coated may be one obtained by applying a surface treatment such as a phosphate treatment, a chromate treatment, a composite oxide treatment or the like to the metal surface of the metal material and a car body molded therefrom, or may be a substrate to be coated having a coating film.

As the above substrate to be coated having the coating film, there can be mentioned a substrate which is subjected to a surface treatment as desired and has an undercoating film formed thereon. In particular, a car body having an undercoating film formed by an electrodeposition coating is preferable, and a car body having an undercoating film formed by a cationic electrodeposition coating is more preferable.

The substrate to be coated may be one obtained by subjecting the surface of plastic such as plastic material and automobile part molded therefrom to surface treatment, primer coating or the like as desired. Further, the plastic material and the metal material may be combined. Since the thermosetting resin composition of the present invention can be made low-temperature curable, it can also be suitably used as a paint for plastics.

The method of applying the thermosetting coating is not particularly limited, and examples thereof include an air spray coating, an airless spray coating, a rotary atomization coating, a curtain coating and the like, and air spray coating, rotary atomization coating, and the like are preferable. At the time of coating, electrostatic application may be performed if desired. By the above coating method, a wet coating film can be formed from the water-borne coating composition.

The wet coating film can be cured by heating. The curing can be carried out by a known heating means, for example, a drying oven such as an air-heating furnace, an electric furnace, an infrared induction heating furnace or the like. The wet coating film is preferably cured by heating at a temperature in the range of about 80 to about 180° C., more preferably about 100 to about 170° C., and even more preferably about 120 to about 160° C., and preferably for about 10 to about 60 minutes, and more preferably for about 15 to about 40 minutes. It is also preferable in that it can cope with low temperature curing at 80 to 140° C. The present invention is also a cured film cured in this way.

When the thermosetting resin composition of the present invention is used in the field of coatings, sufficient curing performance such as smoothness, water resistance, acid resistance, etc. is required. On the other hand, when it is used in the field of adhesives, pressure sensitive adhesives and the like, high curing performance required for coatings is not required. The thermosetting resin composition of the present invention can be brought to a level that can be used as a coating, but compositions which do not reach such a level may be usable in the fields of adhesives, pressure sensitive adhesives and the like.

The present invention is a cured film formed by three-dimensionally crosslinking the thermosetting resin composition described above.
Such a cured film has sufficient performance so that it can be used as a coating/adhesive.

EXAMPLES

Hereinafter, the present disclosure will be explained with reference to examples. However, the present disclosure is not limited to these examples. In addition, "part(s)" means "part(s) by weight" in the examples.

Synthesis Example 1

Ethylene glycol monoacetoacetate monomethacrylate 54 parts, 58 parts of t-butyl acrylate, 38 parts of potassium carbonate, 2 parts of 18-crown-6 ether and 112 parts of tetrahydrofuran were mixed and stirred at 50° C. for 3 hours. After completion of the reaction, cyclohexane and water were added and washed with water. The organic layer was neutralized with a saturated aqueous solution of ammonium chloride and washed twice with water, and the obtained organic layer was concentrated under reduced pressure to obtain a monomer A.

Synthesis Example 2

Ethylene glycol monoacetoacetate monomethacrylate 54 parts, 32 parts of t-butyl acrylate, 38 parts of potassium carbonate, 2 parts of 18-crown-6 ether and 112 parts of tetrahydrofuran were mixed and stirred at 50° C. for 3 hours. After completion of the reaction, cyclohexane and water were added and washed with water. The organic layer was neutralized with a saturated aqueous solution of ammonium chloride and washed twice with water, and the obtained organic layer was concentrated under reduced pressure to obtain a monomer B.

Synthesis Example 3

Sulfuric acid 13 parts, 63 parts of magnesium sulfate, and 260 parts of methylene chloride were mixed and stirred at room temperature for 15 minutes. Then, 30 parts of 2-methacryloyloxyethyl succinic acid (Kyoeisha Chemical Co., Ltd., Light Ester HO-MS) and 50 parts of t-butyl alcohol were added and stirred for 18 hours. After completion of the reaction, the mixture was neutralized with aqueous solution of sodium hydrogen carbonate and washed twice with water. The obtained organic layer was concentrated under reduced pressure to obtain a monomer C.

Synthesis Example 4

N-butyl methacrylate (Kyoeisha Chemical Co., Ltd., Light Ester NB) 200 parts, 175 parts of monomer A, 90 parts of hydroxyethyl methacrylate (Kyoeisha Chemical Co., Ltd., Light Ester HO-250) and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.
Aromatic hydrocarbon (T-SOL 100) 490 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution A.

Synthesis Example 5

N-butyl methacrylate (Kyoeisha Chemical Co., Ltd., Light Ester NB) 200 parts, 242 parts of monomer B, 90 parts of hydroxyethyl methacrylate (Kyoeisha Chemical Co., Ltd., Light Ester HO-250) and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.
Aromatic hydrocarbon (T-SOL 100) 557 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution B.

Synthesis Example 6

N-butyl methacrylate (Kyoeisha Chemical Co., Ltd., Light Ester NB) 200 parts, 202 parts of monomer C, 90 parts of hydroxyethyl methacrylate (Kyoeisha Chemical Co., Ltd., Light Ester HO-250) and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.

Aromatic hydrocarbon (T-SOL 100) 517 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution C.

Synthesis Example 7

N-butyl methacrylate (Kyoeisha Chemical Co., Ltd., Light Ester NB) 240 parts, 120 parts of t-butyl methacrylate (Kyoeisha Chemical Co., Ltd., Light Ester TB), 110 parts of hydroxyethyl methacrylate (Kyoeisha Chemical Co., Ltd., Light Ester HO-250) and 30 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution. Aromatic hydrocarbon (T-SOL 100) 250 parts and 250 parts of cyclohexanone were placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution D.

Physical properties of the resins obtained by the above synthesis examples are shown in Table 1 below.

TABLE 1

|  | Solid content/% | Mn | Mw | Mw/Mn |
|---|---|---|---|---|
| Polymer solution A | 50 | 5,300 | 14,300 | 2.70 |
| Polymer solution B | 50 | 5,000 | 13,600 | 2.70 |
| Polymer solution C | 50 | 4,500 | 14,600 | 3.22 |
| Polymer solution D | 50 | 4,700 | 8,800 | 1.88 |

Example 1

Phenolsulfonic acid (PHS) was mixed with polymer solution A so as to be 2 wt % relative to the solid content of the polymer solution. A coating film of 400 μm was formed by WET using an applicator, and cured at 120° C. for 30 minutes.

Thereafter, a gel fraction was measured, and a xylene rubbing test and a rigid body pendulum test with the prepared liquid were carried out.

Example 2

Phenolsulfonic acid (PHS) was mixed with polymer solution B so as to be 2 wt % relative to the solid content of the polymer solution. A coating film of 400 μm was formed by WET using an applicator, and cured at 120° C. for 30 minutes.

Thereafter, a gel fraction was measured, and a xylene rubbing test and a rigid body pendulum test with the prepared liquid were carried out.

Example 3

Phenolsulfonic acid (PHS) was mixed with polymer solution C so as to be 2 wt % relative to the solid content of the polymer solution. A coating film of 400 μm was formed by WET using an applicator, and cured at 120° C. for 30 minutes.

Thereafter, a gel fraction was measured, and a xylene rubbing test and a rigid body pendulum test with the prepared liquid were carried out.

Comparative Example 1

Phenolsulfonic acid (PHS) was mixed with polymer solution D so as to be 2 wt % relative to the solid content of the polymer solution. A coating film of 400 μm was formed by WET using an applicator, and cured at 140° C. for 30 minutes.

Thereafter, a gel fraction was measured, and a xylene rubbing test and a rigid body pendulum test with the prepared liquid were carried out.

Comparative Example 2

Phenolsulfonic acid (PHS) was mixed with polymer solution D so as to be 2 wt % relative to the solid content of the polymer solution. A coating film of 400 μm was formed by WET using an applicator, and cured at 120° C. for 30 minutes.

Thereafter, a gel fraction was measured, and a xylene rubbing test and a rigid body pendulum test with the prepared liquid were carried out.

These results are shown in Table 2.

TABLE 2

Figure 2:
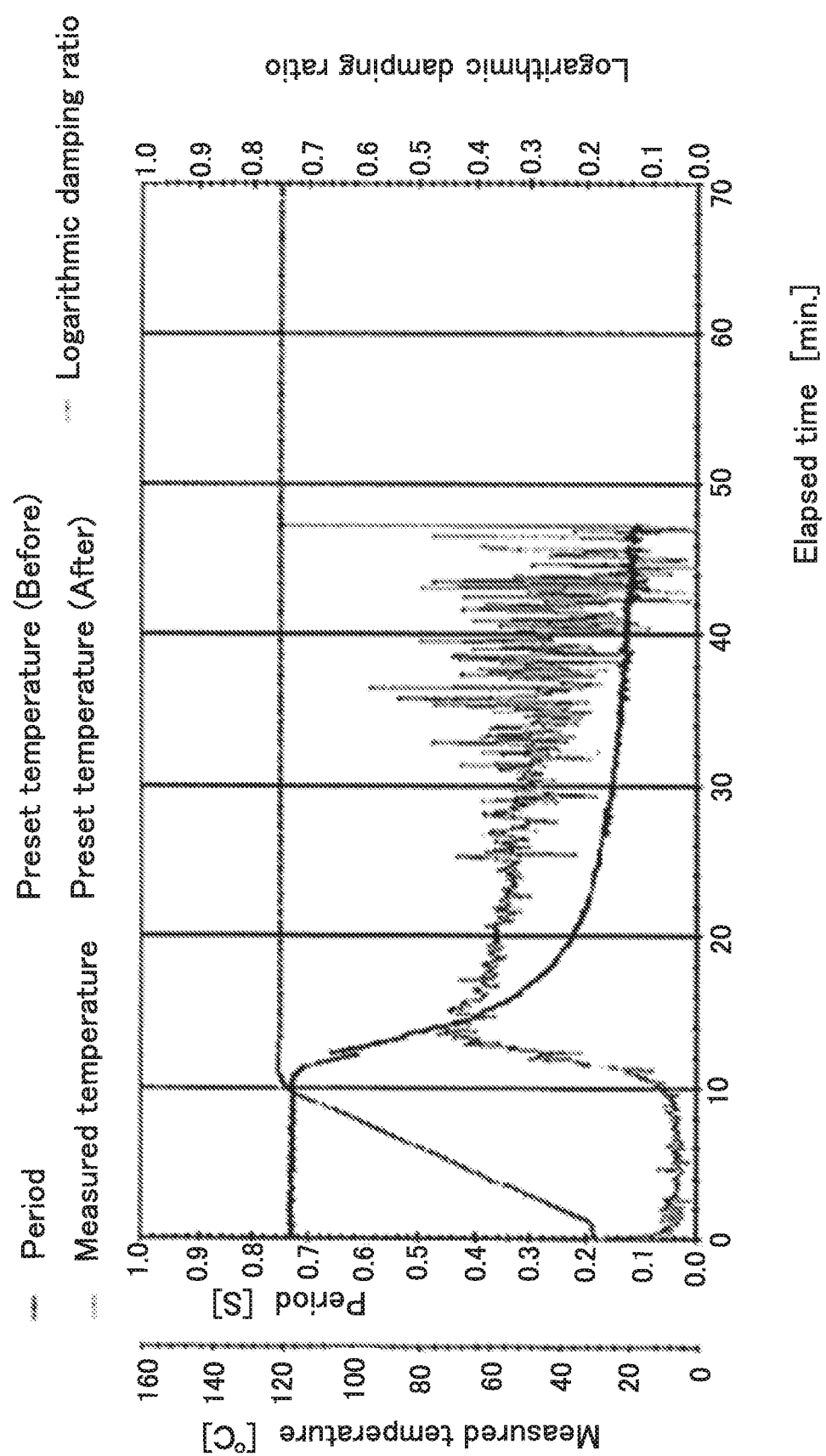
FIG. 2 is a rigid body pendulum data at 120° C. of Example 2.
Figure 3:
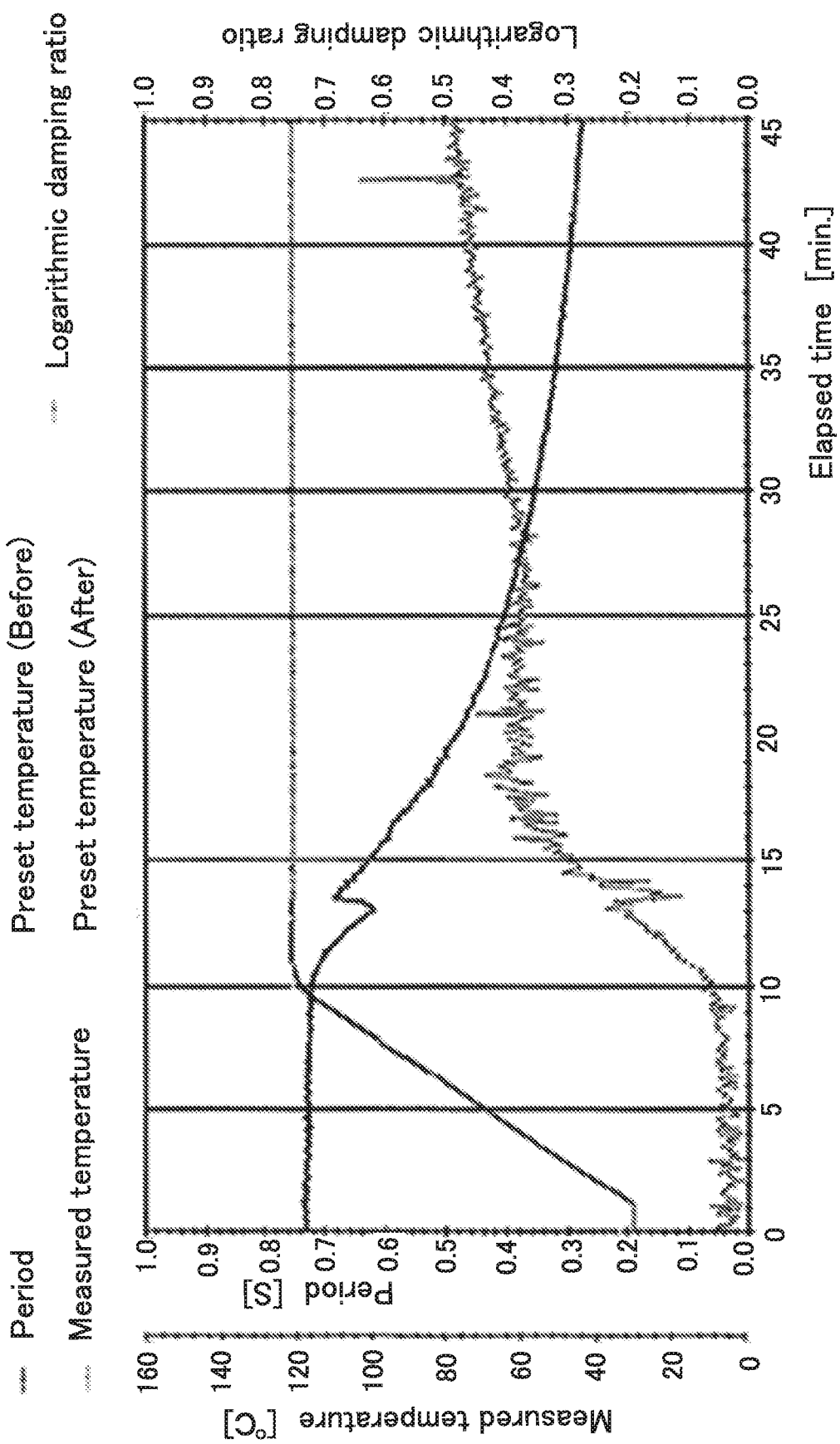
FIG. 3 is a rigid body pendulum data at 120° C. of Example 3.
Figure 4:
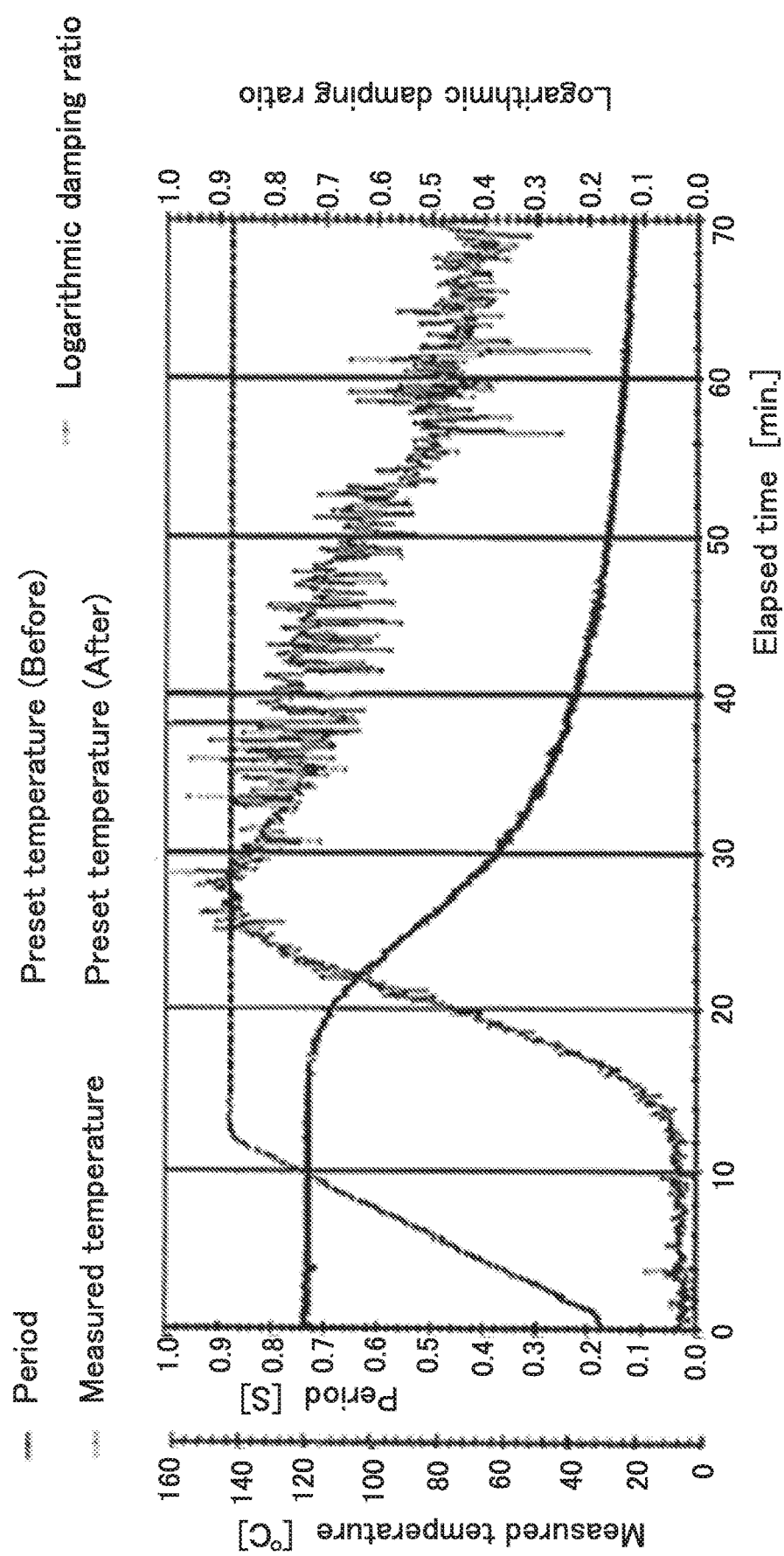
FIG. 4 is a rigid body pendulum data at 140° C. of Comparative Example 1.
Figure 5:
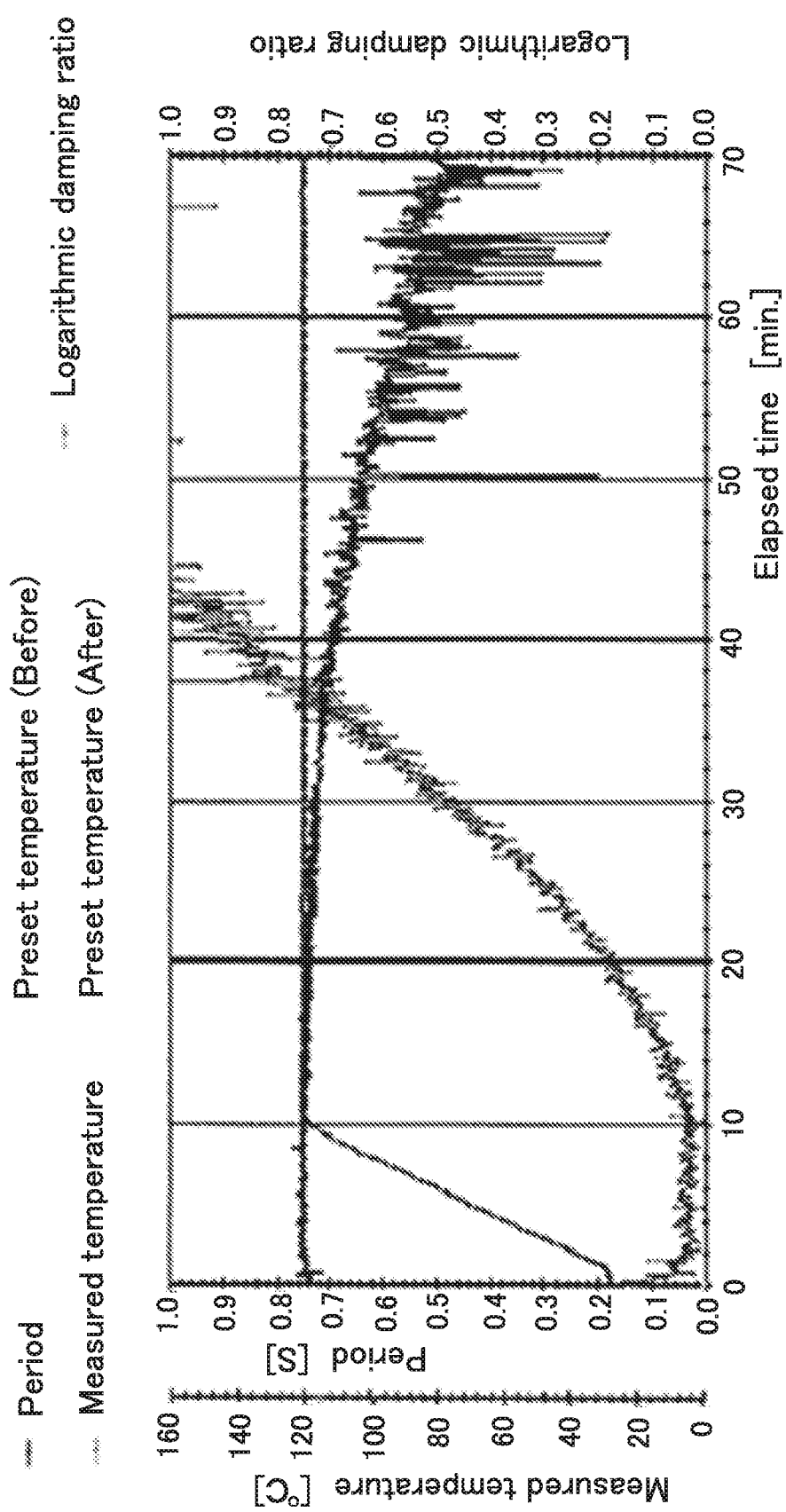
FIG. 5 is a rigid body pendulum data at 120° C. of Comparative Example 2.

|  | Example 1 | Example 2 | Example 3 | Comparative Example 1 | Comparative Example 2 |
|---|---|---|---|---|---|
| Polymer solution A | 100 |  |  |  |  |
| Polymer solution B |  | 100 |  |  |  |
| Polymer solution C |  |  | 100 |  |  |
| Polymer solution D |  |  |  | 100 | 100 |
| PHS | 1.5 | 1.5 | 1.5 | 1.5 | 1.5 |
| Curing temperature | 120° C. | 120° C. | 120° C. | 140° C. | 120° C. |
| Curing time | 30 min. | 30 min. | 30 min. | 30 min. | 30 min. |
| Gel fraction/% | ◎ | ◎ | ◎ | ◎ | Δ |
| Xylene rubbing | ◎ | ◎ | ◎ | ◎ | X |
| Appearance of coating film | No abnormality | No abnormality | No abnormality | With foaming | — |
| Rigid body pendulum | FIG. 1 | FIG. 2 | FIG. 3 | FIG. 4 | FIG. 5 |

The polymer obtained by using the unsaturated group-containing ester compound of the present invention can obtain good effectiveness even at curing at a low temperature of 120° C. and is also excellent in performances such as xylene rubbing. On the other hand, in the case of the polymers of Comparative Examples 1 and 2 in which the unsaturated group-containing ester compound of the present invention is not used, it is possible to perform curing by transesterification at 140° C., but not at 120° C. The polymer of the present invention is preferable in that it can be cured at a low temperature.

From the results in Table 2, it was revealed that the thermosetting resin compositions of Examples 1 to 3 did not cause deterioration of appearance due to foaming, and also had excellent effects in this respect.

Synthesis Example 8

N-butyl methacrylate (Kyoeisha Chemical Co., Ltd., Light Ester NB) 200 parts, 175 parts of monomer A, 100 parts of 4-hydroxybuthyl acrylate and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.
Aromatic hydrocarbon (T-SOL 100) 500 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution E.

Synthesis Example 9

Monomer A 200 parts, 117 parts of 4-hydroxybuthyl acrylate and 17 parts of styrene were mixed to prepare a monomer mixture solution, and 17 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution. Aromatic hydrocarbon (T-SOL 100) 234 parts and 117 parts of propylene glycol monomethyl ether were placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution F.

Synthesis Example 10

N-butyl methacrylate (Kyoeisha Chemical Co., Ltd., Light Ester NB) 200 parts, 175 parts of monomer A, 137 parts of 1,4-cyclohexane dimethanol monoacrylate and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution. Aromatic hydrocarbon (T-SOL 100) 537 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution G.

Physical properties of the resins obtained by the above synthesis examples are shown in Table 3 below.

TABLE 3

| | Solid content/% | Mn | Mw | Mw/Mn |
|---|---|---|---|---|
| Polymer solution E | 50 | 5,500 | 14,600 | 2.68 |
| Polymer solution F | 50 | 3,000 | 9,400 | 3.10 |
| Polymer solution G | 50 | 4,900 | 12,400 | 2.55 |

Example 4

Phenolsulfonic acid (PHS) was mixed with polymer solution E so as to be 2 wt % relative to the solid content of the polymer solution. A coating film of 400 μm was formed by WET using an applicator, and cured at 100° C. for 30 minutes.
Thereafter, a gel fraction was measured, and a xylene rubbing test and a rigid body pendulum test with the prepared liquid were carried out.

Example 5

Phenolsulfonic acid (PHS) was mixed with polymer solution E so as to be 2 wt % relative to the solid content of the polymer solution. A coating film of 400 μm was formed by WET using an applicator, and cured at 80° C. for 30 minutes.
Thereafter, a gel fraction was measured, and a xylene rubbing test and a rigid body pendulum test with the prepared liquid were carried out.

Example 6

Phenolsulfonic acid (PHS) was mixed with polymer solution F so as to be 2 wt % relative to the solid content of the polymer solution. A coating film of 400 μm was formed by WET using an applicator, and cured at 100° C. for 30 minutes.
Thereafter, a gel fraction was measured, and a xylene rubbing test and a rigid body pendulum test with the prepared liquid were carried out.

Example 7

Phenolsulfonic acid (PHS) was mixed with polymer solution F so as to be 2 wt % relative to the solid content of the polymer solution. A coating film of 400 μm was formed by WET using an applicator, and cured at 80° C. for 30 minutes.
Thereafter, a gel fraction was measured, and a xylene rubbing test and a rigid body pendulum test with the prepared liquid were carried out.

Example 8

Phenolsulfonic acid (PHS) was mixed with polymer solution G so as to be 2 wt % relative to the solid content of the polymer solution. A coating film of 400 μm was formed by WET using an applicator, and cured at 100° C. for 30 minutes.
Thereafter, a gel fraction was measured, and a xylene rubbing test and a rigid body pendulum test with the prepared liquid were carried out.

Example 9

Phenolsulfonic acid (PHS) was mixed with polymer solution G so as to be 2 wt % relative to the solid content of the polymer solution. A coating film of 400 μm was formed by WET using an applicator, and cured at 80° C. for 30 minutes. Thereafter, a gel fraction was measured, and a xylene rubbing test and a rigid body pendulum test with the prepared liquid were carried out.

Example 10

Phenolsulfonic acid (PHS) was mixed with polymer solution A so as to be 2 wt % relative to the solid content of the polymer solution. A coating film of 400 μm was formed by WET using an applicator, and cured at 100° C. for 30 minutes.
Thereafter, a gel fraction was measured, and a xylene rubbing test and a rigid body pendulum test with the prepared liquid were carried out.

Comparative Example 3

Phenolsulfonic acid (PHS) was mixed with polymer solution D so as to be 2 wt % relative to the solid content of the polymer solution. A coating film of 400 μm was formed by WET using an applicator, and cured at 100° C. for 30 minutes.
Thereafter, a gel fraction was measured, and a xylene rubbing test and a rigid body pendulum test with the prepared liquid were carried out.
These results are shown in Table 4.

Synthesis Example 12

N-butyl methacrylate (Kyoeisha Chemical Co., Ltd., Light Ester NB) 245 parts, 110 parts of t-butyl acrylate (Kyoeisha Chemical Co., Ltd., Light Acrylate TB) and 30 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution. Aromatic hydrocarbon 250 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution I.

Physical properties of the resins obtained by the above synthesis examples are shown in Table 5 below.

TABLE 5

|  | Solid content/% | Mn | Mw | Mw/Mn |
|---|---|---|---|---|
| Polymer solution H | 50 | 4,300 | 14,700 | 3.45 |
| Polymer solution I | 50 | 5,400 | 10,400 | 1.93 |

TABLE 4

Figure 6:
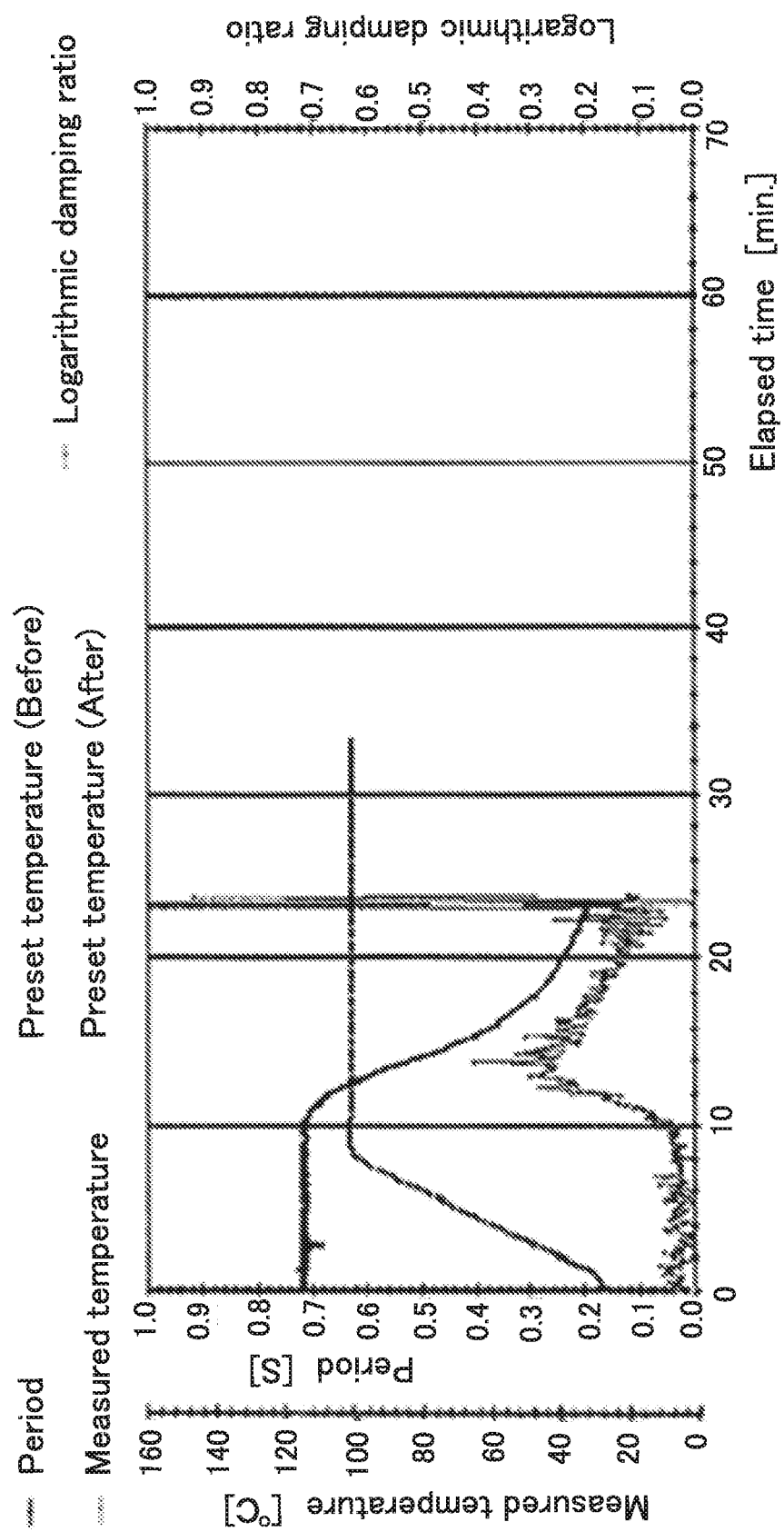
FIG. 6 is a rigid body pendulum data at 100° C. of Example 4.
Figure 7:
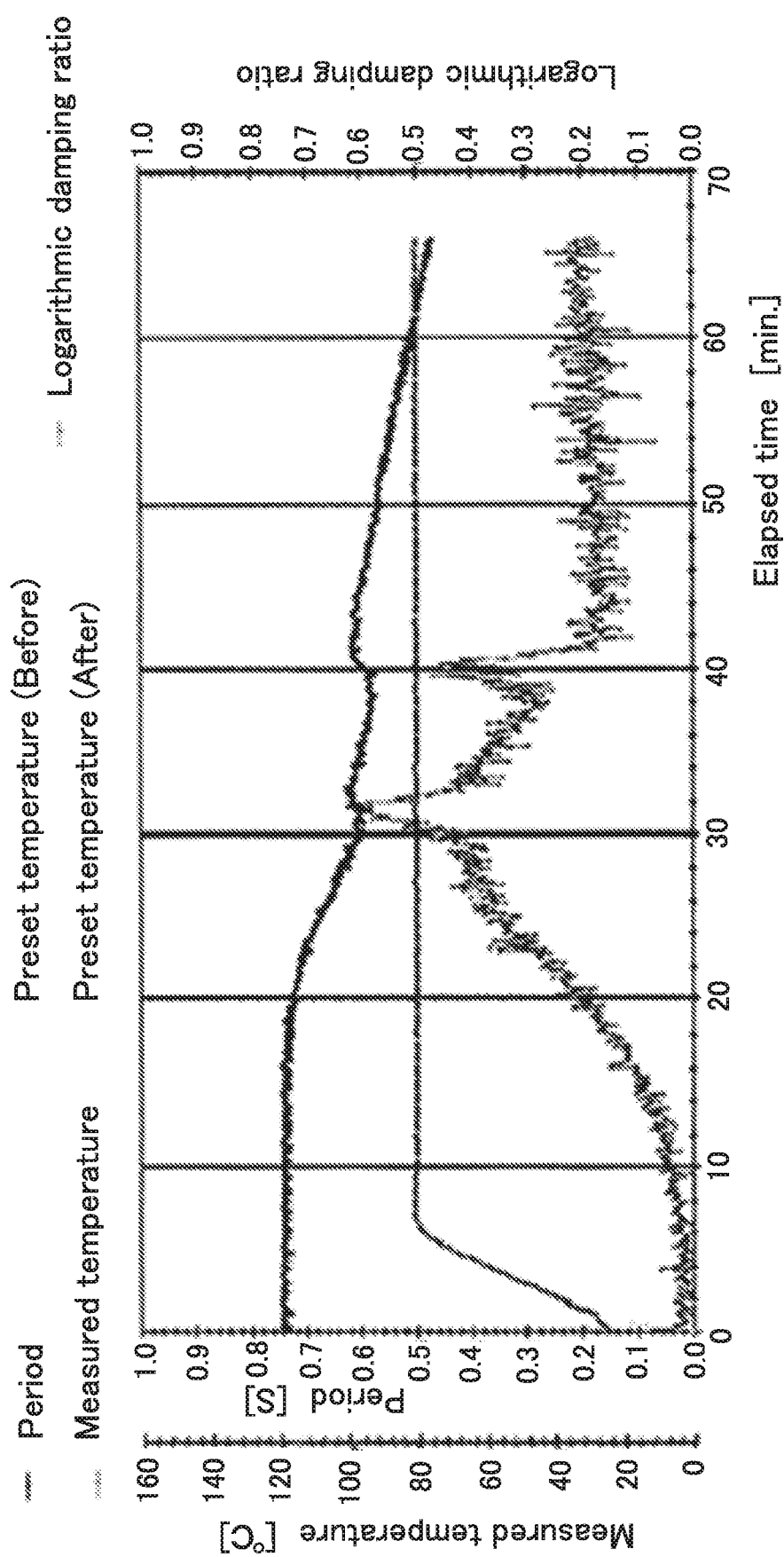
FIG. 7 is a rigid body pendulum data at 80° C. of Example 5.
Figure 8:
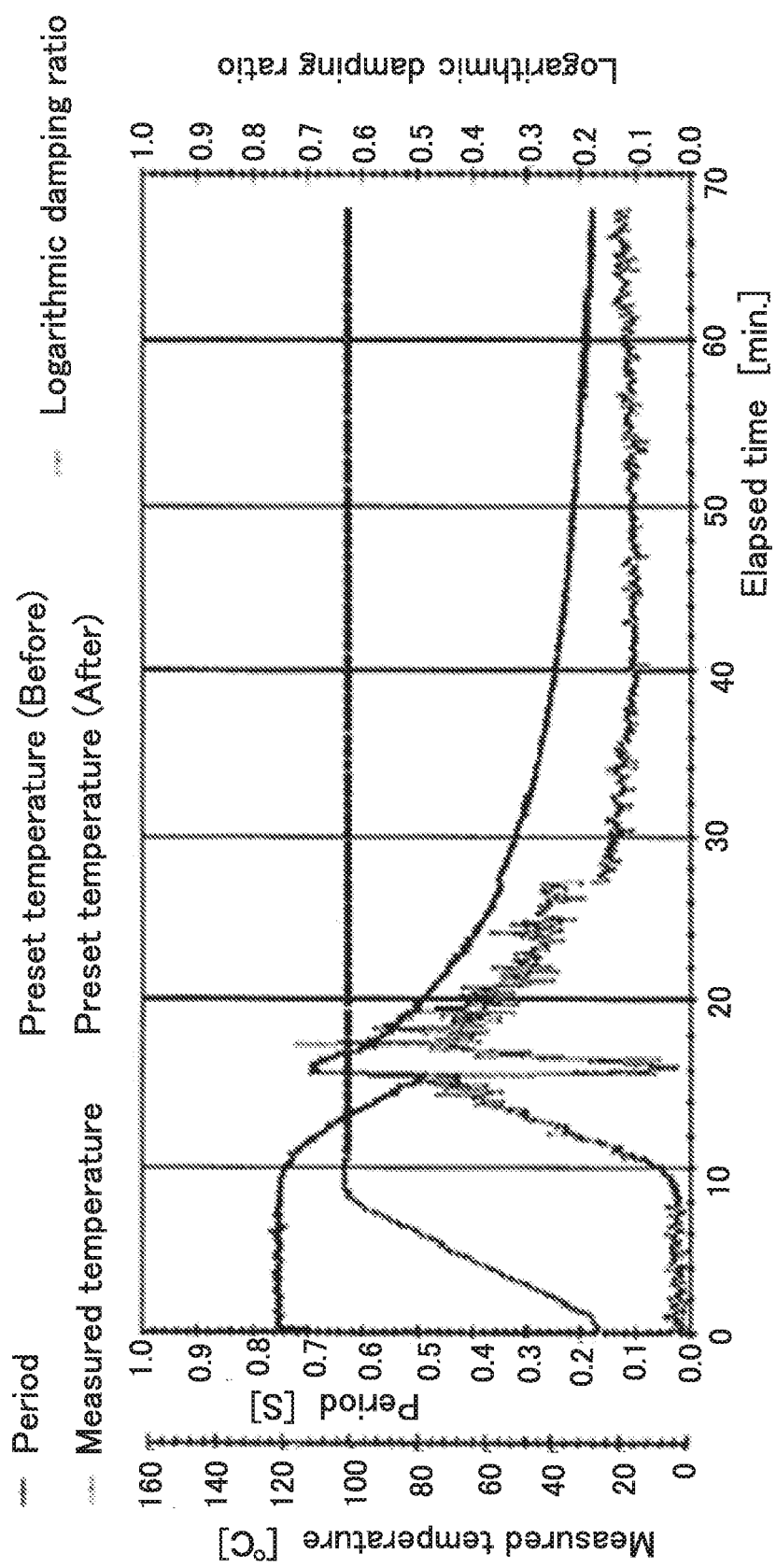
FIG. 8 is a rigid body pendulum data at 100° C. of Example 6.
Figure 9:
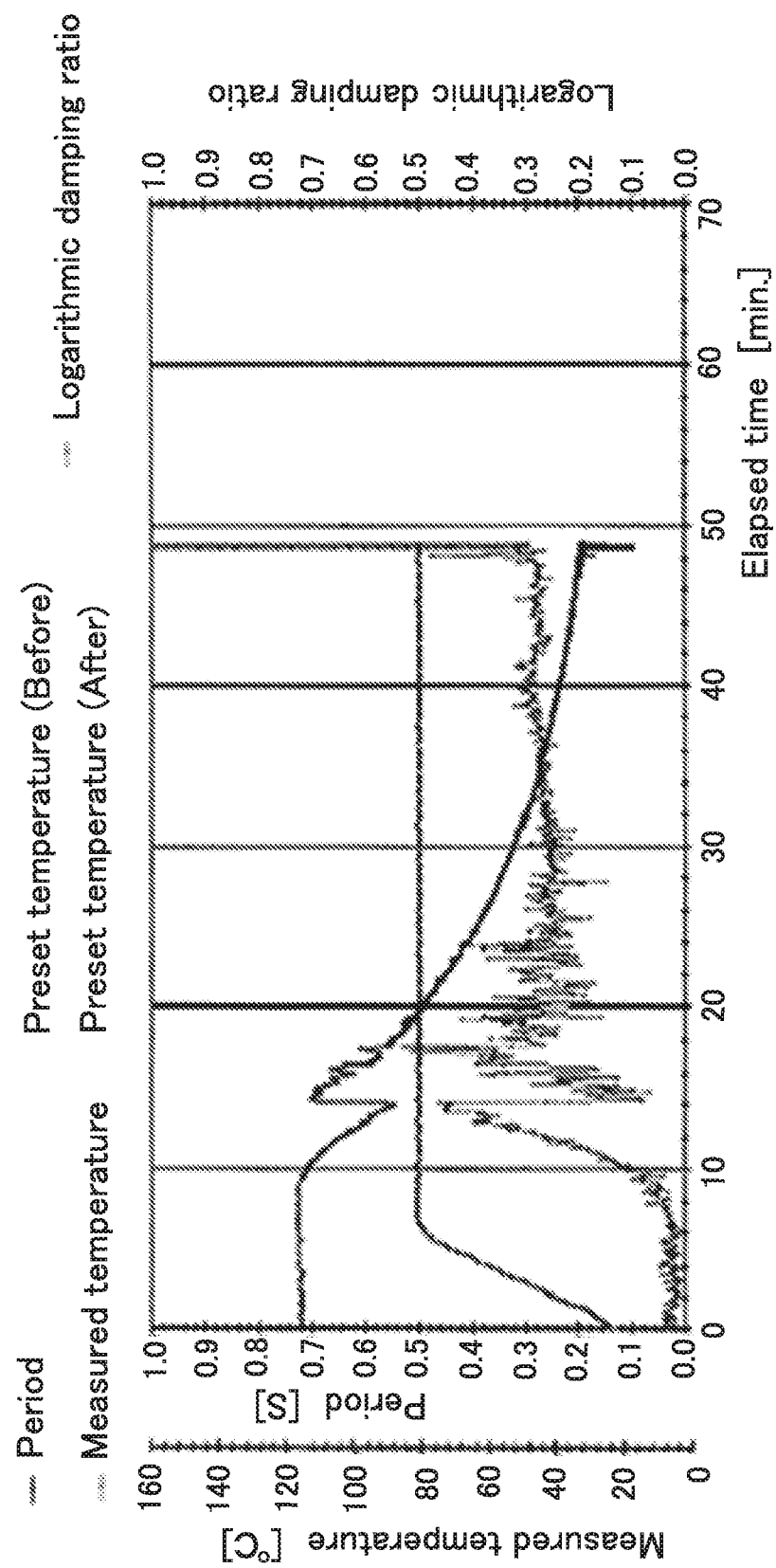
FIG. 9 is a rigid body pendulum data at 80° C. of Example 7.
Figure 10:
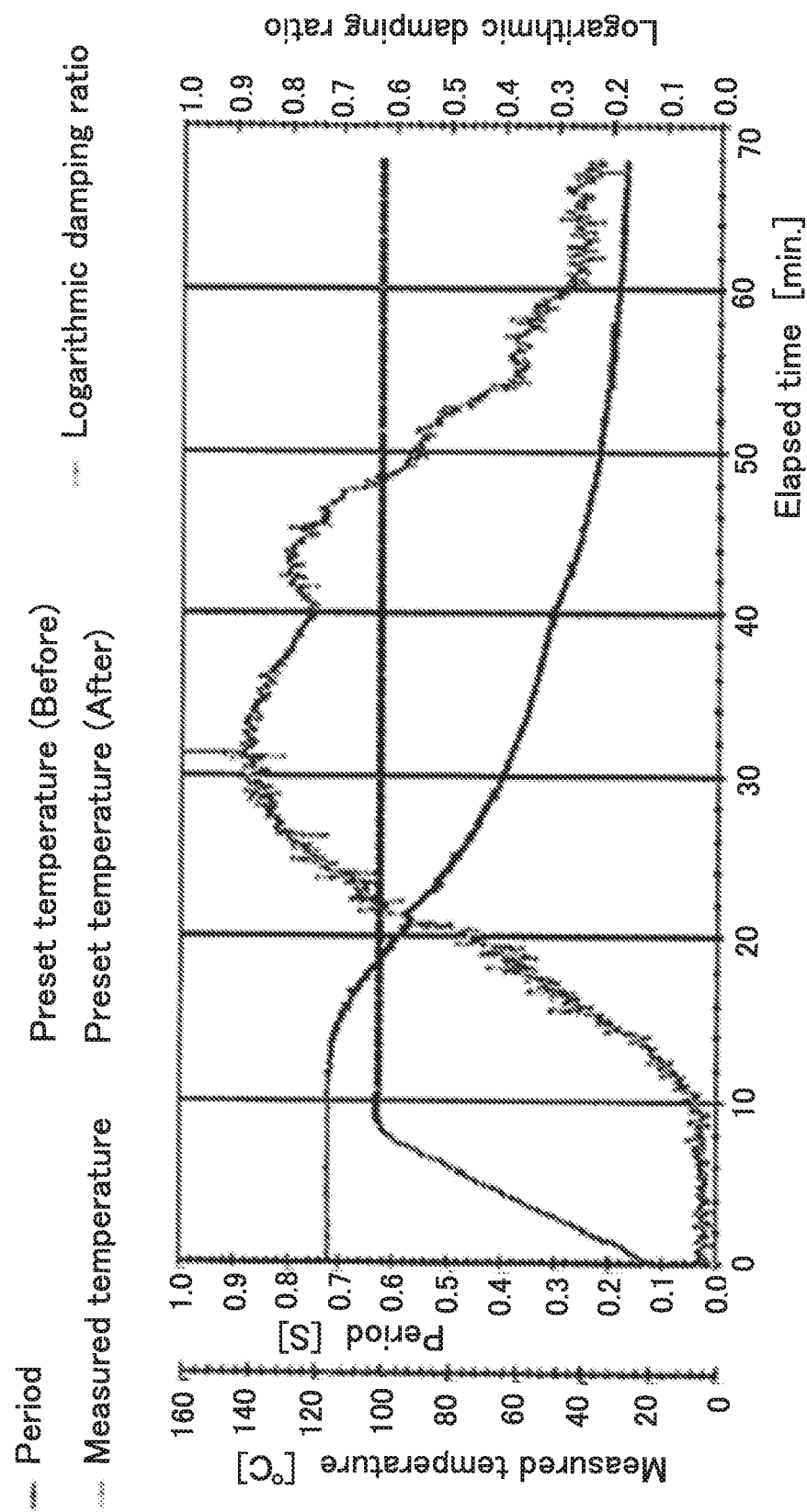
FIG. 10 is a rigid body pendulum data at 100° C. of Example 10.
Figure 11:
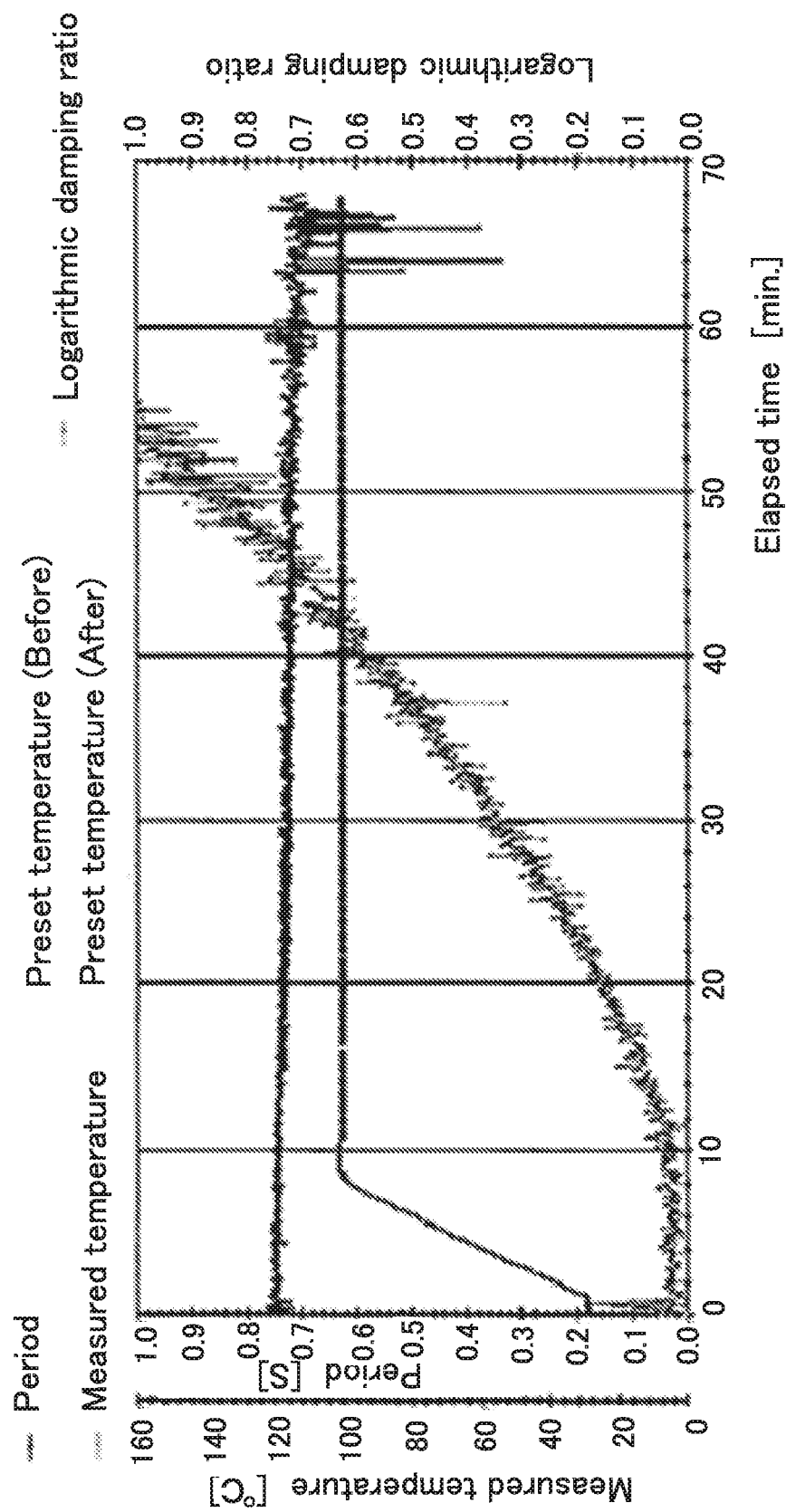
FIG. 11 is a rigid body pendulum data at 100° C. of Comparative Example 3.

|  | Ex. 4 | Ex. 5 | Ex. 6 | Ex. 7 | Ex. 8 | Ex. 9 | Ex. 10 | Compar. Ex. 3 |
|---|---|---|---|---|---|---|---|---|
| Polymer solution E | 100 | 100 |  |  |  |  |  |  |
| Polymer solution F |  |  | 100 | 100 |  |  |  |  |
| Polymer solution G |  |  |  |  | 100 | 100 |  |  |
| Polymer solution A |  |  |  |  |  |  | 100 |  |
| Polymer solution D |  |  |  |  |  |  |  | 100 |
| PHS | 1.5 | 1.5 | 1.5 | 1.5 | 1.5 | 1.5 | 1.5 | 1.5 |
| Curing temperature | 100° C. | 80° C. | 100° C. | 80° C. | 100° C. | 80° C. | 100° C. | 100° C. |
| Curing time | 30 min. | 30 min. | 30 min. | 30 min. | 30 min. | 30 min. | 30 min. | 30 min. |
| Gel fraction/% | ◎ | ○ | ◎ | ◎ | ◎ | Δ | ○ | X |
| Xylene rubbing | ◎ | X | ◎ | ◎ | ○ | X | X | X |
| Rigid body pendulum | FIG. 6 | FIG. 7 | FIG. 8 | FIG. 9 |  |  | FIG. 10 | FIG. 11 |

From the results of Examples 4 to 10 and Comparative Example 3 described above, it was revealed that when the hydroxyl group-containing monomer represented by the general formula (4) is used, the obtained polymer can be cured at a low temperature of 80 to 100° C.

Synthesis Example 11

N-butyl methacrylate (Kyoeisha Chemical Co., Ltd., Light Ester NB) 150 parts, 130 parts of monomer A, and 20 parts of styrene were mixed to prepare a monomer solution. 2,2'-azobis(2,4-dimethylvaleronitrile) (Wako Pure Chemical Industries, V-65) 15 parts was dissolved in an aromatic hydrocarbon (T-SOL 100) to prepare an initiator solution. Aromatic hydrocarbon (T-SOL 100) 300 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution H.

Example 11

Phenolsulfonic acid (PHS) was mixed with 100 parts of polymer solution H and 14 parts of 50% 1,6-hexanediol PGME solution so as to be 2 wt % relative to the solid content of the polymer solution. A coating film of 400 μm was formed by WET using an applicator, and cured at 140° C. for 30 minutes. Thereafter, a gel fraction was measured.

Comparative Example 4

Phenolsulfonic acid (PHS) was mixed with 100 parts of polymer solution I and 14 parts of 50% 1,6-hexanediol PGME solution so as to be 2 wt % relative to the solid content of the polymer solution. A coating film of 400 μm was formed by WET using an applicator, and cured at 140° C. for 30 minutes. Thereafter, a gel fraction was measured. These results are shown in Table 6.

TABLE 6

|  | Example 11 | Comparative Example 4 |
|---|---|---|
| Polymer solution H | 100 |  |
| Polymer solution I |  | 100 |
| 1,6-hexanediol PGME solution | 14 | 14 |
| PHS | 1.7 | 1.7 |
| Curing temperature | 140° C. | 140° C. |
| Curing time | 30 min. | 30 min. |
| Gel fraction/% | ◎ | X |

From the above Example 11 and Comparative Example 4, it was clear that a curable composition using the composition comprising the unsaturated group-containing ester compound of the present invention and the hydroxyl group-containing compound can also obtain a good curing ability.

Synthesis Example 13

Ethylene glycol monoacetoacetate monomethacrylate 54 parts, 58 parts of n-butyl acrylate, 38 parts of potassium carbonate, 2 parts of 18-crown-6 ether and 112 parts of tetrahydrofuran were mixed and stirred at 50° C. for 3 hours. After completion of the reaction, cyclohexane and water were added and washed with water. The organic layer was neutralized with a saturated aqueous solution of ammonium chloride and washed twice with water, and the obtained organic layer was concentrated under reduced pressure to obtain a monomer D.

Synthesis Example 14

Ethylene glycol monoacetoacetate monomethacrylate 60 parts, 48 parts of methyl acrylate, 48 parts of potassium carbonate, 3 parts of 18-crown-6 ether and 108 parts of tetrahydrofuran were mixed and stirred at 50° C. for 3 hours. After completion of the reaction, cyclohexane and water were added and washed with water. The organic layer was neutralized with a saturated aqueous solution of ammonium chloride and washed twice with water, and the obtained organic layer was concentrated under reduced pressure to obtain a monomer E.

Synthesis Example 15

N-butyl methacrylate (Kyoeisha Chemical Co., Ltd., Light Ester NB) 200 parts, 175 parts of monomer D, 90 parts of 4-hydroxybuthyl acrylate and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.
Aromatic hydrocarbon (T-SOL 100) 490 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution J.

Synthesis Example 16

N-butyl methacrylate (Kyoeisha Chemical Co., Ltd., Light Ester NB) 200 parts, 175 parts of monomer E, 90 parts of 4-hydroxybuthyl acrylate and 25 parts of styrene were mixed to prepare a monomer mixture solution, and 25 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution.
Aromatic hydrocarbon (T-SOL 100) 490 parts was placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a polymer solution K.

Synthesis Example 17

N-butyl methacrylate (Kyoeisha Chemical Co., Ltd., Light Ester NB) 240 parts, 110 parts of hydroxyethyl methacrylate (Kyoeisha Chemical Co., Ltd., Light Ester HO-250) and 30 parts of styrene were mixed to prepare a monomer mixture solution, and 19 parts of 2,2'-azobis(2,4-dimethylvaleronitrile) (Wako Pure Chemical Industries, V-65) as an initiator was dissolved in an aromatic hydrocarbon (T-SOL 100) to prepare an initiator solution. Aromatic hydrocarbon (T-SOL 100) 190 parts and 190 parts of cyclohexanone were placed in a stirrable flask, and the monomer solution and the initiator solution were added dropwise while nitrogen was enclosed. The polymerization temperature at this time was 100° C. The dropwise addition was carried out for 2 hours, and further aging was carried out at 100° C. for 4 hours to obtain a comparative polymer solution L.

Physical properties of the resins obtained by the above synthesis examples are shown in Table 7 below.

TABLE 7

|  | Solid content/% | Mn | Mw | Mw/Mn |
|---|---|---|---|---|
| Polymer solution J | 50 | 4,200 | 13,600 | 3.23 |
| Polymer solution K | 50 | 5,200 | 14,400 | 2.79 |
| Polymer solution L | 50 | 5,300 | 9,400 | 1.78 |

Example 12

Phenolsulfonic acid (PHS) was mixed with polymer solution J so as to be 2 wt % relative to the solid content of the polymer solution. A coating film of 400 μm was formed by WET using an applicator, and cured at 140° C. for 30 minutes. Thereafter, a gel fraction was measured and a rigid body pendulum test with the prepared liquid was carried out.

Examples 13 to 16

A coating film was formed and cured by following the same manner as in Example 12 except that dioctyltin dilaurate or Aluminum Chelate M (product name, Kawaken Fine Chemicals Co., Ltd.) was added at the blending amount shown in Table 8 to polymer solution J or K instead of phenolsulfonic acid (PHS). Thereafter, a gel fraction was measured and a rigid body pendulum test with the prepared liquid was carried out.

Comparative Example 5

Phenolsulfonic acid (PHS) was mixed with polymer solution L so as to be 2 wt % relative to the solid content of the polymer solution. A coating film of 400 μm was formed by WET using an applicator, and cured at 140° C. for 30 minutes. Thereafter, a gel fraction was measured and a rigid body pendulum test with the prepared liquid was carried out. These results are shown in Table 8.

Comparative Example 6

A coating film was formed and cured by following the same manner as in Comparative Example 5 except that dioctyltin dilaurate was added (3 wt %) instead of phenolsulfonic acid (PHS). Thereafter, a gel fraction was measured and a rigid body pendulum test with the prepared liquid was carried out.

Ion exchanged water 400 parts and 10 parts of isopropyl alcohol were placed in a stirrable flask, and the monomer solution and the initiator solution were added dropwise while nitrogen was enclosed to carry out polymerization. The polymerization temperature at this time was 80° C. The dropwise addition was carried out for 2 hours, and further aging was carried out at 80° C. for 4 hours to obtain polymer solution M.

Example 17

Phenolsulfonic acid (PHS) was mixed with polymer solution M so as to be 2 wt % relative to the solid content of the

TABLE 8

Figure 12:
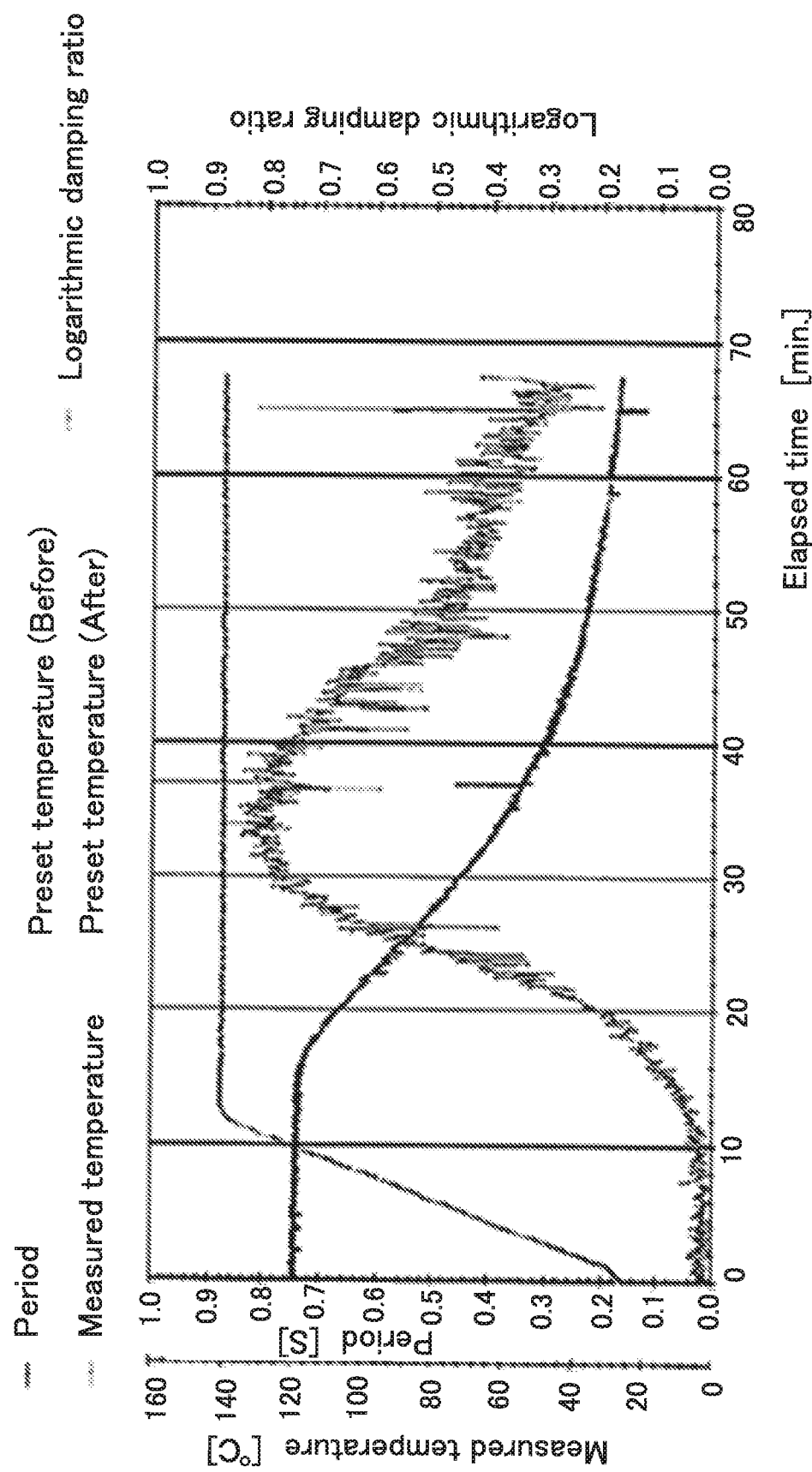
FIG. 12 is a rigid body pendulum data at 140° C. of Example 12.
Figure 13:
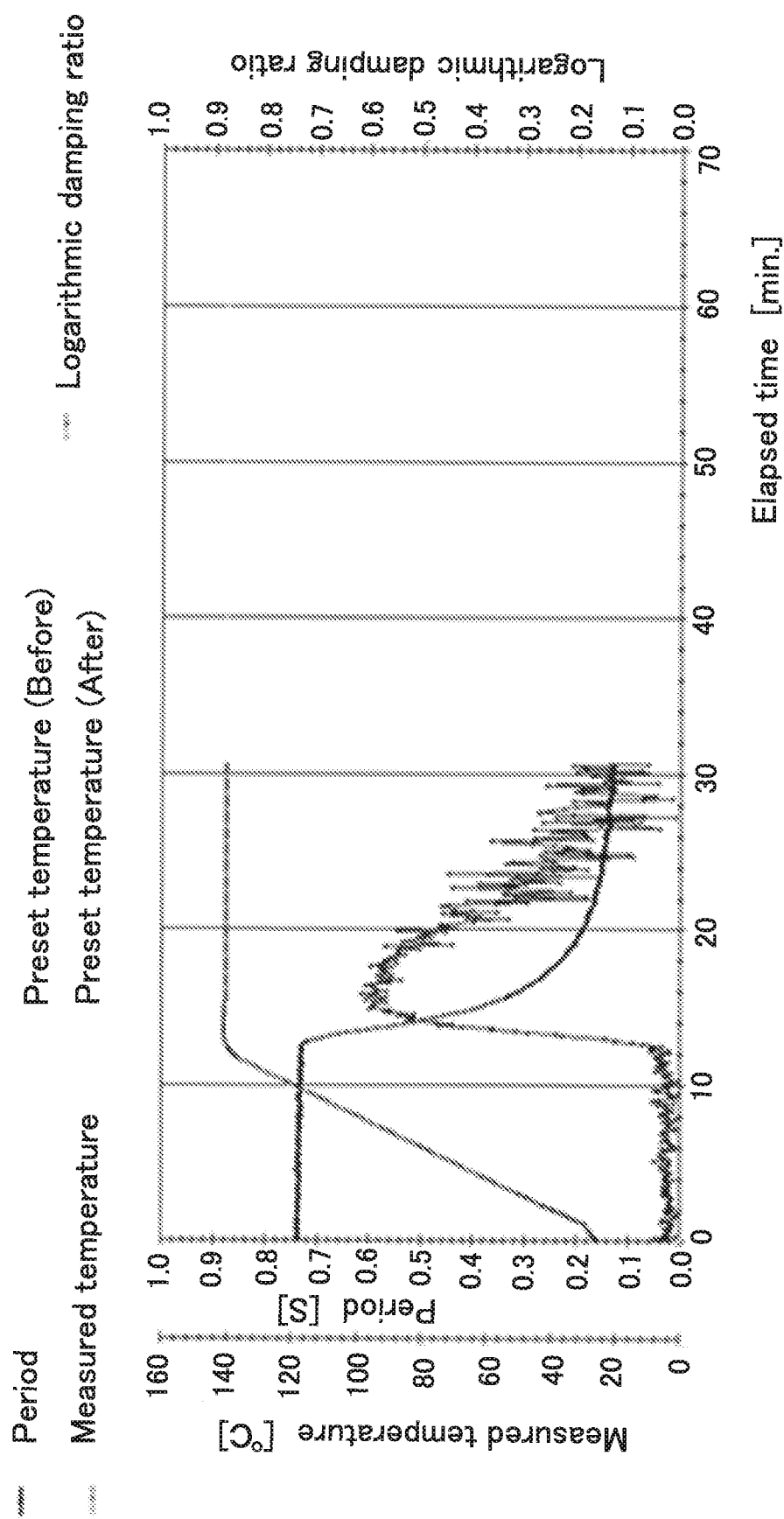
FIG. 13 is a rigid body pendulum data at 140° C. of Example 13.
Figure 14:
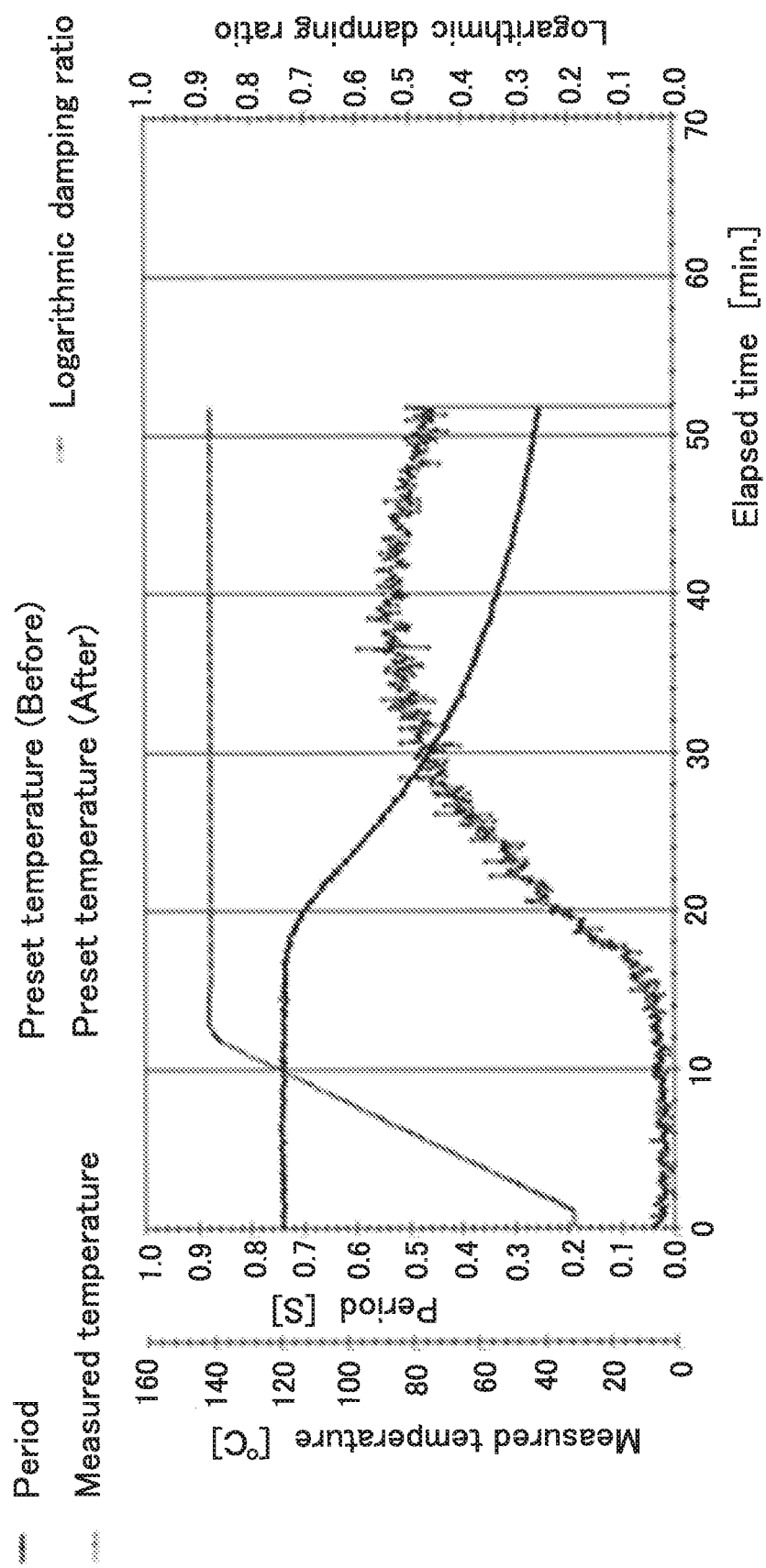
FIG. 14 is a rigid body pendulum data at 140° C. of Example 14.
Figure 15:
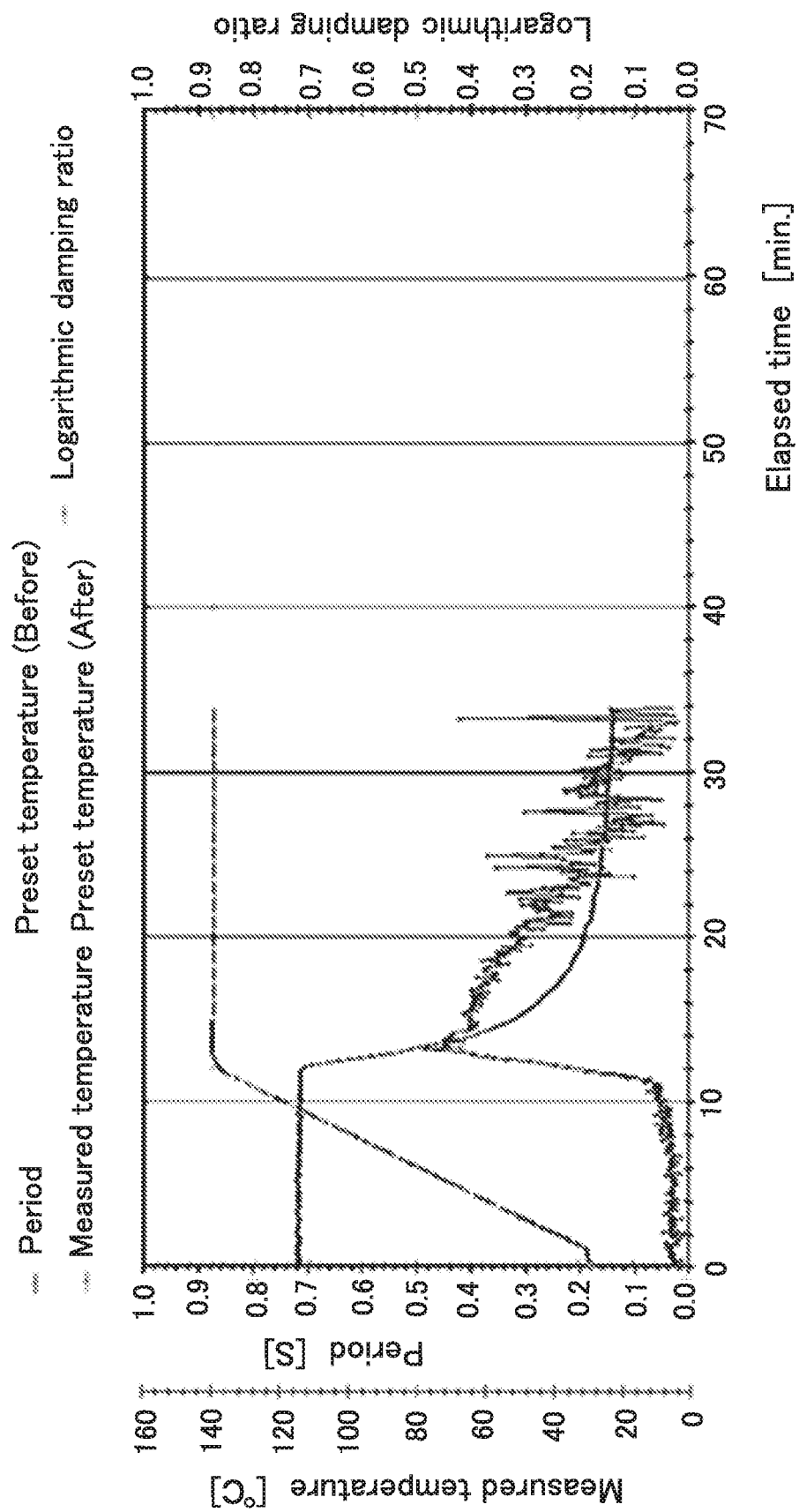
FIG. 15 is a rigid body pendulum data at 140° C. of Example 15.
Figure 16:
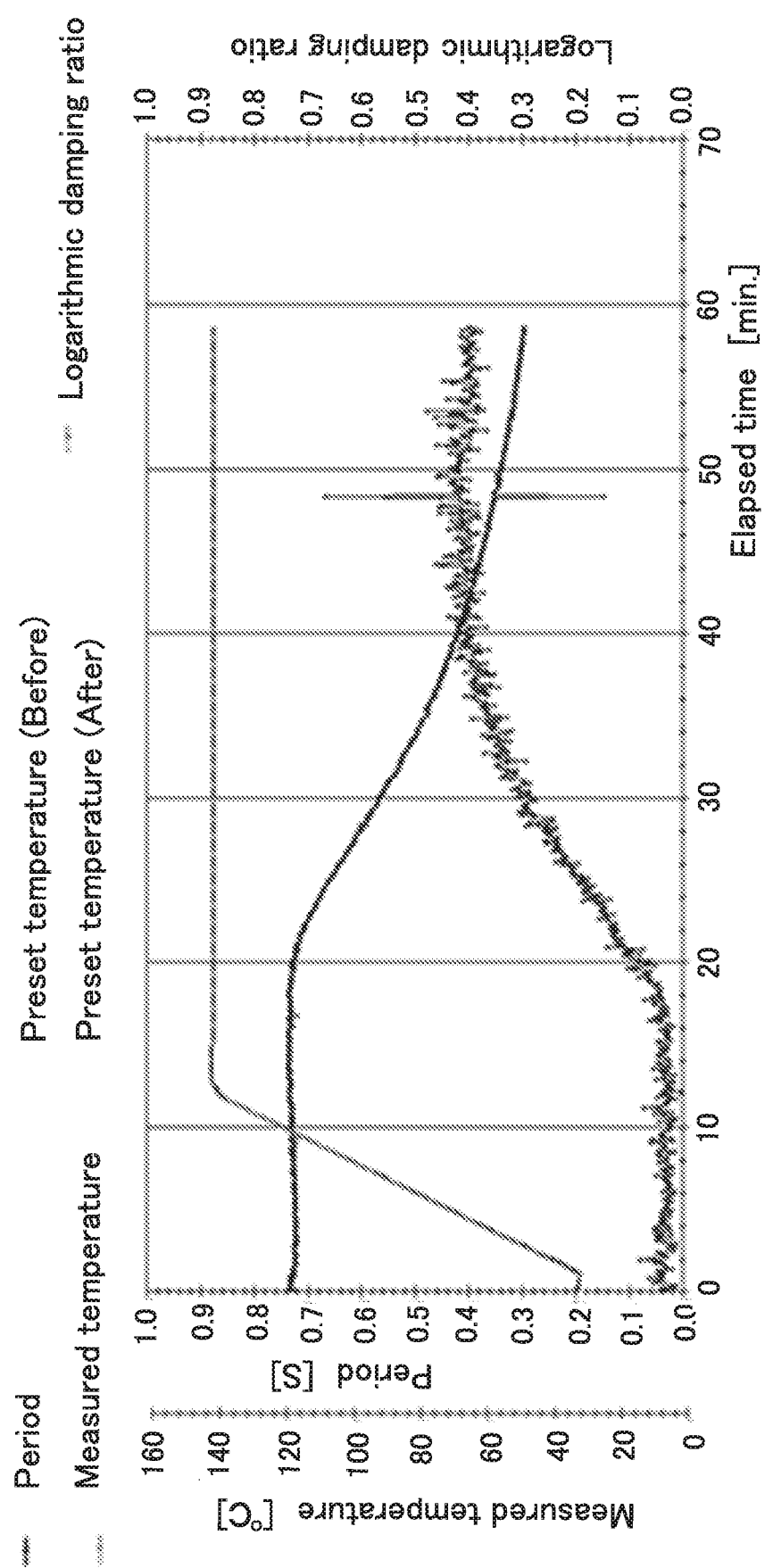
FIG. 16 is a rigid body pendulum data at 140° C. of Example 16.
Figure 17:
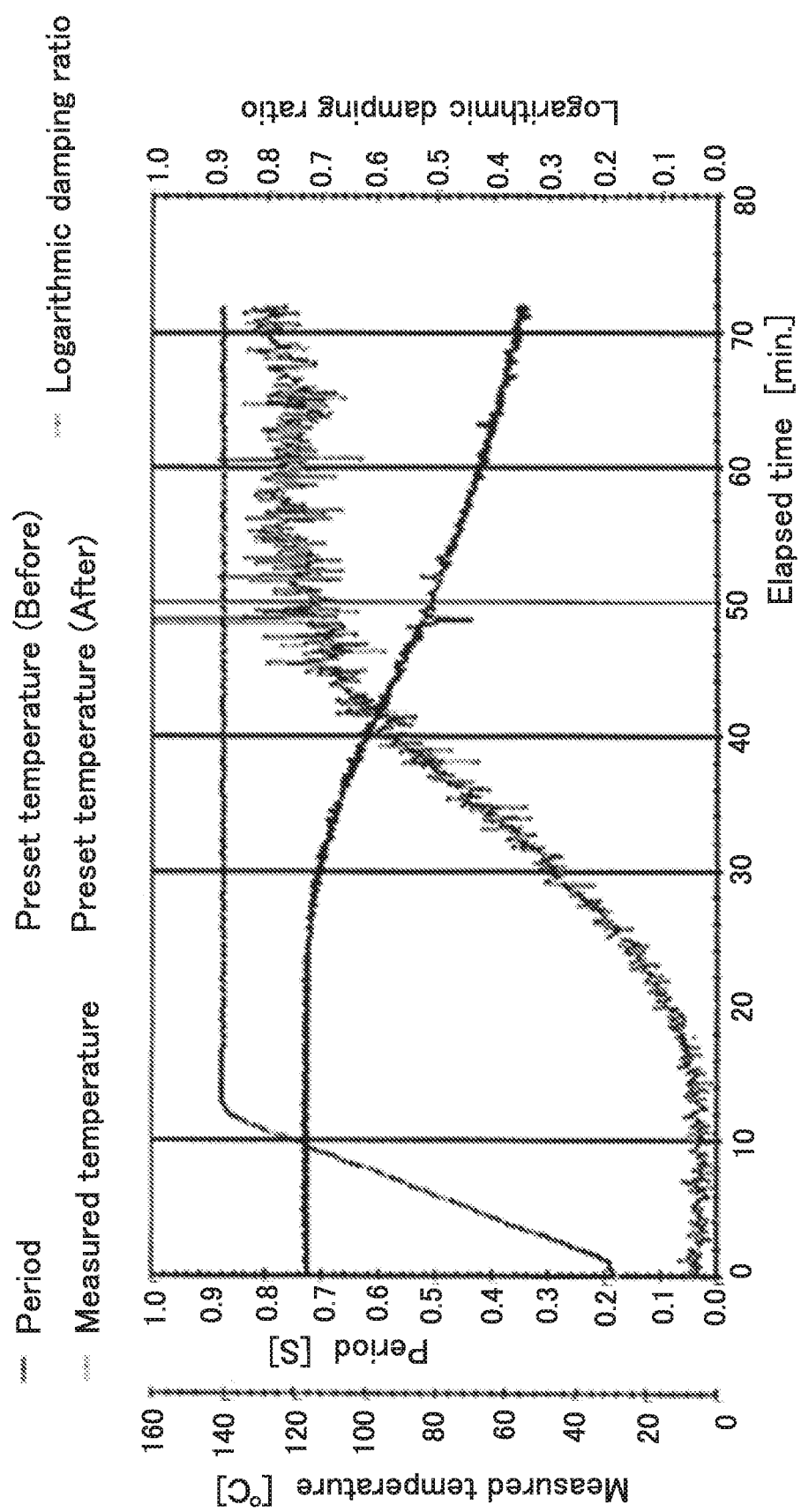
FIG. 17 is a rigid body pendulum data at 140° C. of Comparative Example 5.
Figure 18:
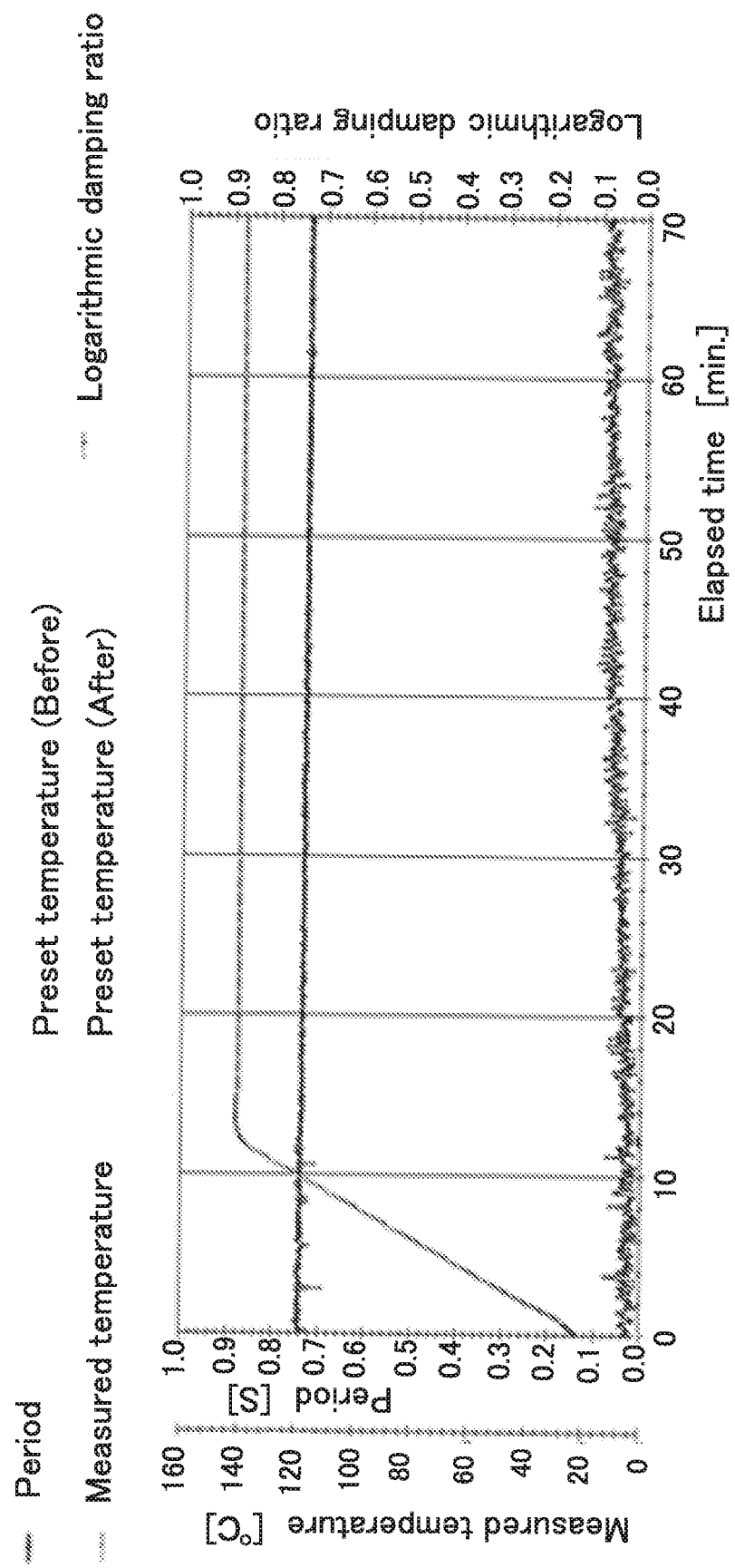
FIG. 18 is a rigid body pendulum data at 140° C. of Comparative Example 6.

|  | Ex. 12 | Ex. 13 | Ex. 14 | Ex. 15 | Ex. 16 | Compar. Ex. 5 | Compar. Ex. 6 |
| --- | --- | --- | --- | --- | --- | --- | --- |
| Polymer solution J | 100 | 100 | 100 |  |  |  |  |
| Polymer solution K |  |  |  | 100 | 100 |  |  |
| Polymer solution L |  |  |  |  |  | 100 | 100 |
| PHS | 1.5 |  |  |  |  | 1.5 |  |
| Dioctyltin dilaurate |  | 1.5 |  | 1.5 |  |  | 1.5 |
| Aluminum Chelate M |  |  | 1.5 |  | 1.5 |  |  |
| Curing temperature | 140° C. | 140° C. | 140° C. | 140° C. | 140° C. | 140° C. | 140° C. |
| Curing time | 30 min. | 30 min. | 30 min. | 30 min. | 30 min. | 30 min. | 30 min. |
| Gel fraction/% | ⊚ | ⊚ | ⊚ | ⊚ | ⊚ | X | X |
| Xylene rubbing | X | ⊚ | ○ | ⊚ | ⊚ | X | X |
| Rigid body pendulum | FIG. 12 | FIG. 13 | FIG. 14 | FIG. 15 | FIG. 16 | FIG. 17 | FIG. 18 |

Aluminum Chelate M: Kawaken Fine Chemicals Co., Ltd.: Aluminum alkylacetylacetonate diisopropoxide From the results of Example 12 and Comparative Example 5, also in the case that the polymer obtained from the unsaturated group-containing ester compound of the present invention containing a primary alkyl ester which shows lower transesterification reactivity than a tertiary alkyl ester was used, constant gel fraction could be obtained at 140° C. From such a result, it is clear that even when the unsaturated group-containing ester compound of the present invention having a primary alkyl ester, suitable results can be obtained.

Furthermore, from the results of Examples 13 to 16, when a tin compound or an aluminum compound is used as a catalyst, its catalytic activity is particularly excellent. Specifically, even if the alkyl ester group is a primary alkyl ester group, good curing performance can be obtained, and also the physical properties of the obtained cured film become satisfactory Such an effect is an effect obtained only when a monomer having a specific structure as in the present invention is used. As in Comparative Example 6, when the alkyl ester group based on methacrylate is used, such an effect cannot be obtained.

Synthesis Example 18

N-butyl methacrylate (Kyoeisha Chemical Co., Ltd., Light Ester NB) 240 parts, 202 parts of monomer A, 110 parts of hydroxyethyl methacrylate (Kyoeisha Chemical Co., Ltd., Light Ester HO-250), 30 parts of styrene, and 15 parts of reactive emulsifier (DKS Co. Ltd. Aquaron KH-10) were mixed. Then, 200 parts of ion exchanged water was mixed with the obtained solution and emulsification was carried out for 1 hour at room temperature using a homomixer to prepare a monomer emulsion. Ammonium peroxodisulfate 15 parts and 10 parts of sodium bisulfite as an initiator were dissolved in ion exchanged water to prepare an initiator solution.

polymer solution. A coating film of 400 μm was formed by WET using an applicator, and cured at 140° C. for 30 minutes. Thereafter, a gel fraction was measured and a xylene rubbing test was carried out.
These results are shown in Table 9.

TABLE 9

|  | Example 17 |
| --- | --- |
| Polymer solution L | 100 |
| PHS | 1.5 |
| Curing temperature | 140° C. |
| Curing time | 30 min. |
| Gel fraction/% | ⊚ |
| Xylene rubbing | ⊚ |

From the results in Table 9, it is clear that the thermosetting resin composition of the present invention can obtain suitable curing performance at 140° C. even when it is a water-based composition.

The physical properties in the above tables 1 to 9 were measured by the following methods. The gel fraction was determined by dissolving the film obtained in Examples using Soxhlet for 30 minutes in acetone reflux, and measuring the residual weight % of the film as gel fraction. When the gel fraction was 0% to 40%, it was indicated as x, which means a state that the film cannot withstand practical use.
When the gel fraction was 40% to 60%, it was indicated as Δ, which means a state that a certain degree of curing is observed.
When the gel fraction was 60% to 80%, it was indicated as ○, which means a state that the film can withstand practical use.
When the gel fraction was 80% to 100%, it was indicated as ⊚, which means a state that the performance is excellent.
In xylene rubbing, the thermosetting resin of the example was coated on a PET film and rubbed 10 times with medicinal gauze impregnated with xylene, and the surface was observed.

Those that cannot withstand practical use were indicated as x, those that can withstand practical use were indicated as o, and further those with excellent performance were indicated as Ⓞ.

A coating film was formed by applying the thermosetting resin of Examples on PET film so as to have the thickness of cured film to 50 to 60 μm, and then the appearance of the obtained coating film was evaluated by observing.

Rigid Body Pendulum Tester

Using a rigid body pendulum tester (model number RPT-3000 W) manufactured by A & D Corporation, the temperature was raised up to each temperature (80, 100, 120, and 140° C.) at a heating rate of 10° C./min. and held. And the change in the period and the logarithmic damping ratio was obtained. In particular, it was used to check the cured state of the coating film.

Pendulum: FRB-100
Film thickness (WET): 100 μm

When the gel fraction is 40 or more, it is judged that a certain curing reaction occurs, and it is obvious that it has a function as a curable composition.

Those having excellent properties in xylene rubbing and water resistance are also suitable for use in many applications including coatings (especially coatings forming the outermost layer) based on these properties. When high gel fraction is needed but the performance such as xylene rubbing and water resistance is not important, the curable resin composition of the present invention can be used in the fields of pressure sensitive adhesives and adhesives and of the inner layer of multilayer coating films.

From the results of the above examples, it was revealed that the thermosetting resin composition of the present invention has excellent curing performance at low temperature. Therefore, it is obvious that it can suitably be used in applications such as coatings and adhesives.

INDUSTRIAL APPLICABILITY

The unsaturated group-containing ester compound of the present invention can be used as a raw material for a curable composition using a transesterification reaction as a curing reaction. The curable composition can be used as a coating composition, an adhesive composition or the like. In particular, since it can be cured at low temperature, it can also be applied to applications requiring curing at low temperature, such as plastic coating.

The invention claimed is:

1. A thermosetting resin composition comprising a polymer (A) containing a structural unit derived from an unsaturated group-containing ester compound having a chemical structure represented by the following formula (3):

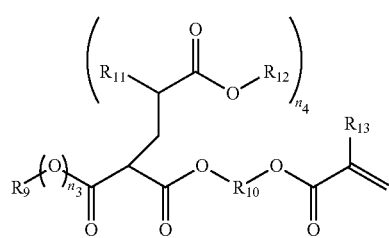

where:
$R_9$ is an alkyl group having 1 to 50 carbon atoms;
$R_{10}$ is an alkylene group with a number of atoms of 44 or less in the main chain, which may have an ester group, an ether group and/or an amide group in the main chain, and may have a side chain;
$R_{11}$ is H or a methyl group;
$R_{12}$ is an alkyl group having 50 or less carbon atoms;
$R_{13}$ is H or a methyl group;
$n_3$ is 0 or 1; and
$n_4$ is 1 or 2;
a hydroxyl group-containing compound (B) with at least two hydroxyl groups; and
a transesterification catalyst (F).

2. The thermosetting resin composition according to claim 1, wherein $R_{12}$ is a tertiary alkyl group.

3. The thermosetting resin composition according to claim 1, wherein the hydroxyl group-containing compound (B) is a polymer containing a structural unit derived from the monomer represented by the following formula (4) in at least a portion thereof:

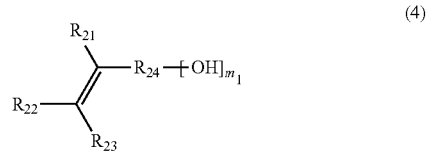

where:
$m_1$ is from 1 to 10;
$R_{21}$, $R_{22}$, and $R_{23}$ are the same or different and each is a hydrogen, an alkyl group, a carboxyl group, an alkyl ester group or a structure represented by the following $R_{24}$-[OH]$m_1$; and
$R_{24}$ is an aliphatic, an alicyclic or an aromatic alkylene group with a number of atoms of 3 to 50 in the main chain, which may have one or more functional groups selected from the group consisting of an ester group, an ether group, an amide group, and a urethane and may have a side chain.

4. A thermosetting resin composition comprising:
a polymer (C) containing a structural unit derived from the unsaturated group-containing ester compound represented by the formula (3):

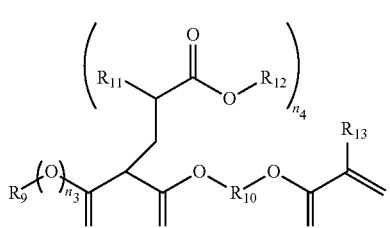

where:
$R_9$ is an alkyl group having 1 to 50 carbon atoms;
$R_{10}$ is an alkylene group with a number of atoms of 44 or less in the main chain, which may have an ester group, an ether group and/or an amide group in the main chain, and may have a side chain;

$R_{11}$ is H or a methyl group;

$R_{12}$ is an alkyl group having 50 or less carbon atoms;

$R_{13}$ is H or a methyl group;

$n_3$ is 0 or 1; and $n_4$ is 1 or 2;

a structural unit derived from a hydroxyl group-containing unsaturated monomer as an essential constituting unit; and a transesterification catalyst (F).

5. The thermosetting resin composition according to claim 4, wherein $R_{12}$ is a tertiary alkyl group.

6. The thermosetting resin composition according to claim 4, wherein the structural unit derived from the hydroxyl group-containing unsaturated monomer contains a structural unit derived from the monomer represented by the following formula (4) in at least a portion thereof:

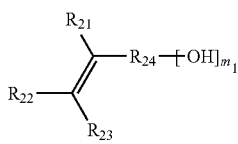

(4)

where:

$m_1$ is from 1 to 10;

$R_{21}$, $R_{22}$, and $R_{23}$ are the same or different and each is a hydrogen, an alkyl group, a carboxyl group, an alkyl ester group or a structure represented by the following $R_{24}$-[OH]$m_1$; and $R_{24}$ is an aliphatic, an alicyclic or an aromatic alkylene group with a number of atoms of 3 to 50 in the main chain, which may have one or more functional groups selected from the group consisting of an ester group, an ether group, an amide group, and a urethane and may have a side chain.

7. A cured film formed by three-dimensionally crosslinking the thermosetting resin composition according to claims 1 or 4.

8. An unsaturated group-containing ester compound having a chemical structure represented by the following formula (3):

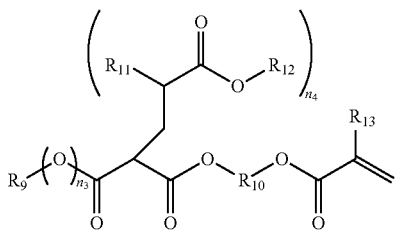

(3)

where:

$R_9$ is an alkyl group having 1 to 50 carbon atoms;

$R_{10}$ is an alkylene group with a number of atoms of 44 or less in the main chain, which may have an ester group, an ether group and/or an amide group in the main chain, and may have a side chain;

$R_{11}$ is H or a methyl group;

$R_{12}$ is an alkyl group having 50 or less carbon atoms;

$R_{13}$ is H or a methyl group;

$n_3$ is 0 or 1; and $n_4$ is 1 or 2.

9. The unsaturated group-containing ester compound according to claim 8, wherein $R_{12}$ is a tertiary alkyl group.

10. A polymer (A) containing a structural unit derived from the unsaturated group-containing ester compound according to claim 8 or 9 in at least a portion thereof.

11. A polymer (C) containing a structural unit derived from the unsaturated group-containing ester compound according to claim 8 or 9 and a structural unit derived from a hydroxyl group-containing unsaturated monomer as an essential constituting unit.

12. The polymer (C) according to claim 9, wherein the structural unit derived from the hydroxyl group-containing unsaturated monomer contains a structural unit derived from the monomer represented by the following formula (4) in at least a portion thereof:

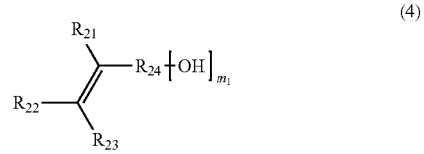

(4)

where:

$m_1$ is from 1 to 10;

$R_{21}$, $R_{22}$, and $R_{23}$ are the same or different and each is a hydrogen, an alkyl group, a carboxyl group, an alkyl ester group or a structure represented by the following $R_{24}$-[OH]$m_1$; and $R_{24}$ is an aliphatic, an alicyclic or an aromatic alkylene group with a number of atoms of 3 to 50 in the main chain, which may have one or more functional groups selected from the group consisting of an ester group, an ether group, an amide group, and a urethane and may have a side chain.

* * * * *